(12) United States Patent
Kohlbrenner et al.

(10) Patent No.: US 7,951,113 B2
(45) Date of Patent: May 31, 2011

(54) DEVICE FOR THE DOSED ADMINISTRATION OF A FLUID PRODUCT COMPRISING A TORSION SPRING DRIVE

(75) Inventors: Philippe Kohlbrenner, Kaltacker (CH); Daniel Kuenzli, Langendorf (CH); Christoph Meier, Utzenstorf (CH); Peter Stettler, Kirchberg (CH); Juergen Wittmann, Burgdorf (CH); Martin Wittwer, Bowil (CH); Edgar Hommann, Grossaffoltern (CH)

(73) Assignee: TecPharma Licensing AG, Burgdorf (CH)

( * ) Notice: Subject to any disclaimer, the term of this patent is extended or adjusted under 35 U.S.C. 154(b) by 779 days.

(21) Appl. No.: 11/769,213

(22) Filed: Jun. 27, 2007

(65) Prior Publication Data
US 2008/0051713 A1  Feb. 28, 2008

Related U.S. Application Data

(63) Continuation of application No. PCT/CH2005/000712, filed on Nov. 30, 2005.

(30) Foreign Application Priority Data

Dec. 31, 2004  (DE) .................. 10 2004 063 644

(51) Int. Cl.
*A61M 5/20* (2006.01)
(52) U.S. Cl. ........ 604/135; 604/131; 604/136; 604/156; 604/138; 604/134; 604/137; 604/157; 604/186; 604/207; 604/208; 604/209; 604/211; 604/218; 604/201; 604/228; 604/232
(58) Field of Classification Search .................. 604/131, 604/136, 156, 232, 138, 134, 135, 137, 157, 604/186, 207–209, 211, 218, 201, 228
See application file for complete search history.

(56) References Cited

U.S. PATENT DOCUMENTS

| | | | | |
|---|---|---|---|---|
| 1,893,221 A | * | 1/1933 | Booth et al. | 205/234 |
| 2,605,766 A | | 8/1952 | Uytenbogaart | |
| 5,092,842 A | * | 3/1992 | Bechtold et al. | 604/135 |
| 5,114,406 A | * | 5/1992 | Gabriel et al. | 604/136 |

(Continued)

FOREIGN PATENT DOCUMENTS

DE  198 38 760  4/2000

(Continued)

*Primary Examiner* — Nicholas D Lucchesi
*Assistant Examiner* — Scott Medway
(74) *Attorney, Agent, or Firm* — Dorsey & Whitney LLP; David E. Bruhn, Esq.

(57) ABSTRACT

A device for administering a fluid product including a housing, a conveying device for the product, a coupling element provided for the drive of the conveying device and which can be rotated about a rotational axis, a first blocking element connected in a rotationally secure manner to the coupling element, a second blocking element detachably engageable with the first blocking element thereby preventing a rotational movement thereof in the drive direction and enabling said rotational movement to take place in the counter dosing direction, a torsion spring connected to the coupling element such that it is stressed by the rotational movement when the blocking elements are engaged in a blocked position and drives the coupling element in a rotary manner after the blocking position is released, and a release element coupled to at least one of the blocking elements such that a release movement of the release element displaces at least one of the blocking elements from the blocked position, the release element also forming a dosing element used to control a product dose.

36 Claims, 12 Drawing Sheets

U.S. PATENT DOCUMENTS

| | | | | |
|---|---|---|---|---|
| 5,378,233 | A * | 1/1995 | Haber et al. | 604/83 |
| 5,383,865 | A * | 1/1995 | Michel | 604/232 |
| 5,591,136 | A * | 1/1997 | Gabriel | 604/211 |
| 5,626,566 | A * | 5/1997 | Petersen et al. | 604/208 |
| 5,743,889 | A * | 4/1998 | Sams | 604/211 |
| 5,827,232 | A * | 10/1998 | Chanoch et al. | 604/208 |
| 6,221,046 | B1 * | 4/2001 | Burroughs et al. | 604/153 |
| 6,547,763 | B2 * | 4/2003 | Steenfeldt-Jensen et al. | 604/181 |
| 6,663,602 | B2 * | 12/2003 | Moller | 604/211 |
| 6,673,049 | B2 * | 1/2004 | Hommann et al. | 604/207 |
| 6,899,699 | B2 * | 5/2005 | Enggaard | 604/246 |
| 6,902,546 | B2 * | 6/2005 | Ferguson | 604/110 |
| 7,316,670 | B2 * | 1/2008 | Graf et al. | 604/207 |
| 7,377,912 | B2 * | 5/2008 | Graf et al. | 604/208 |
| 7,445,613 | B2 * | 11/2008 | Hommann | 604/211 |
| 7,678,085 | B2 * | 3/2010 | Graf | 604/187 |
| 7,740,618 | B2 * | 6/2010 | Markussen | 604/208 |
| 7,771,398 | B2 * | 8/2010 | Knight et al. | 604/208 |
| 7,811,263 | B2 * | 10/2010 | Burren et al. | 604/211 |
| 2001/0037087 | A1 * | 11/2001 | Knauer | 604/137 |
| 2002/0120235 | A1 * | 8/2002 | Enggaard | 604/135 |
| 2004/0054326 | A1 * | 3/2004 | Hommann et al. | 604/131 |

FOREIGN PATENT DOCUMENTS

| | | | |
|---|---|---|---|
| EP | 0 338 806 | | 10/1989 |
| WO | WO 01/10484 | | 2/2001 |
| WO | WO02/30495 | * | 4/2002 |
| WO | WO/02/92153 | * | 5/2002 |
| WO | WO 02/053214 | | 7/2002 |
| WO | WO02/092153 | * | 11/2002 |
| WO | WO2004/002556 | * | 1/2004 |
| WO | WO 2004/002556 | | 1/2004 |
| WO | WO2004/028598 | * | 4/2004 |
| WO | WO 2005/018721 | | 3/2005 |
| WO | WO 2005/046770 | | 5/2005 |

* cited by examiner

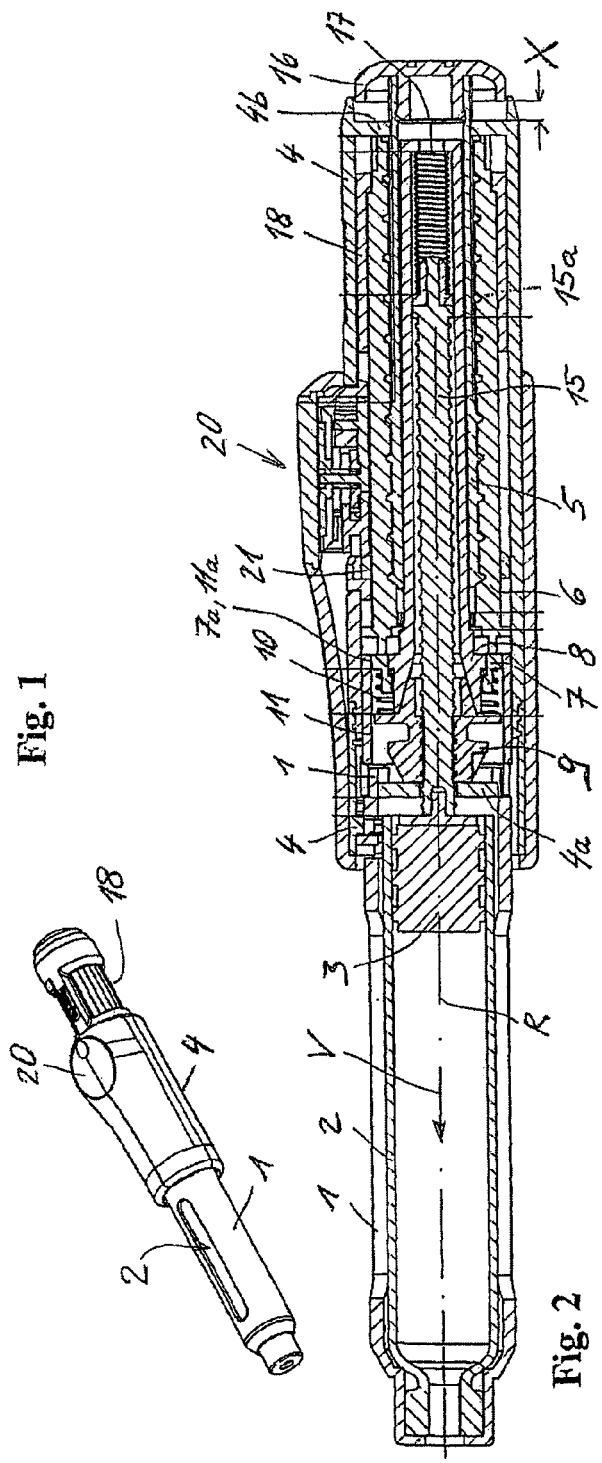
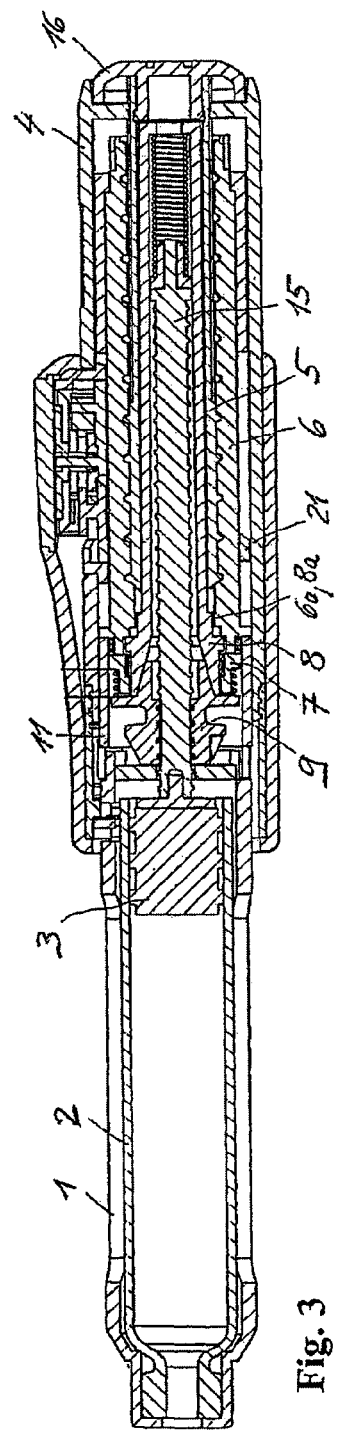
Fig. 1
Fig. 2
Fig. 3

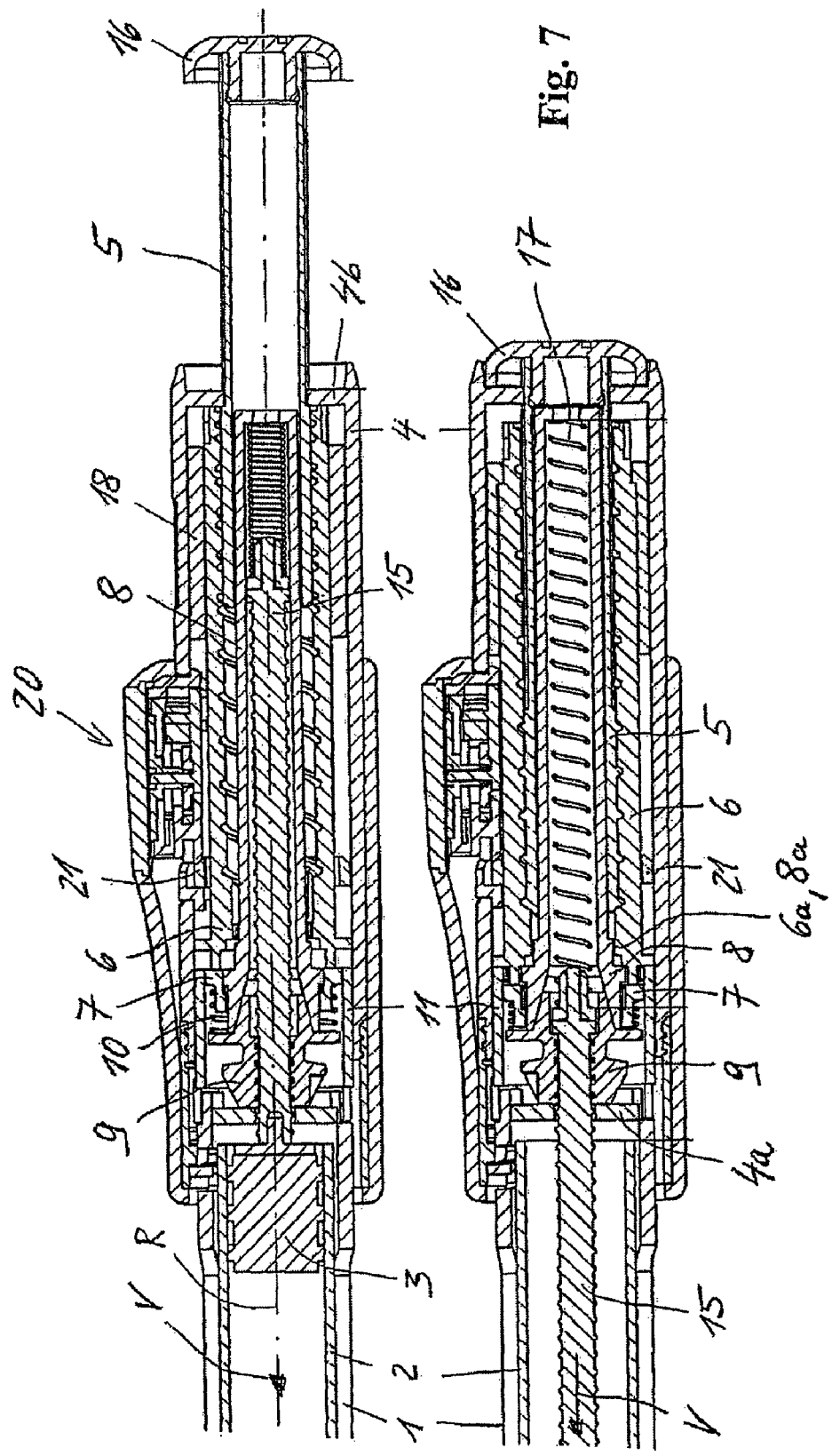

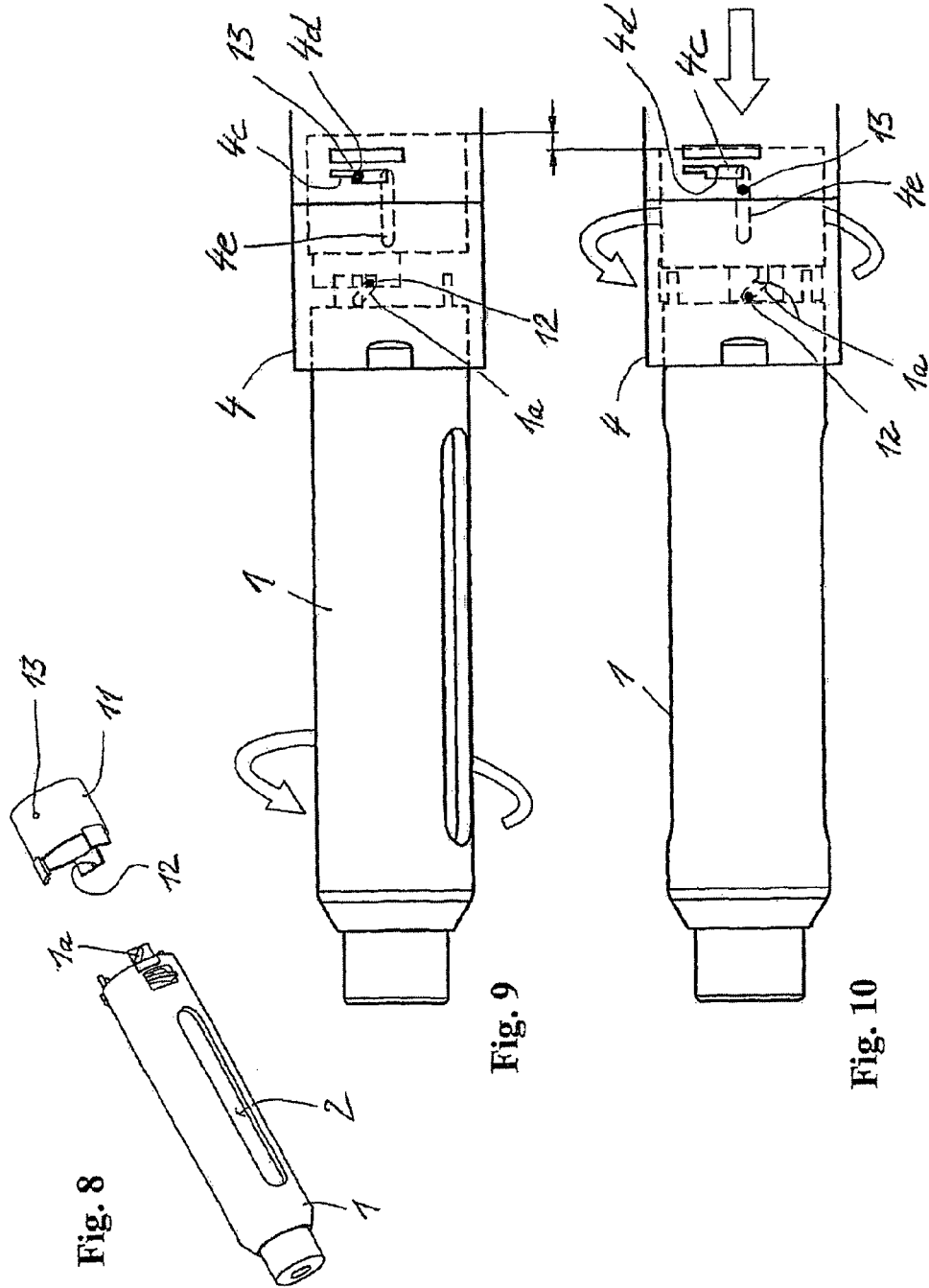

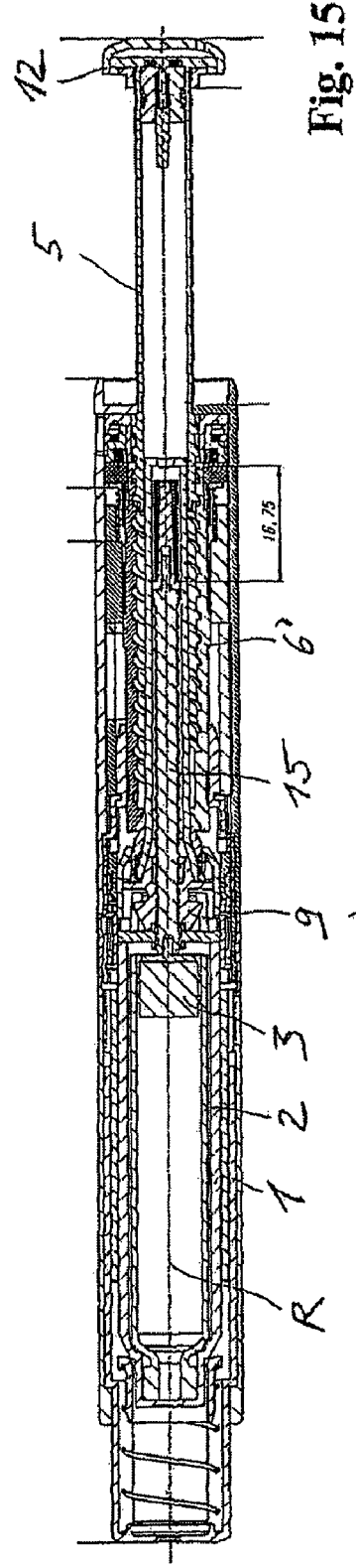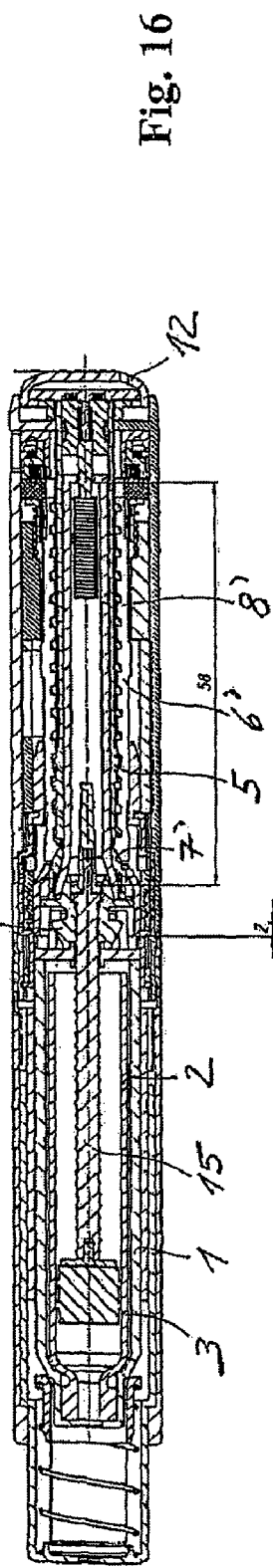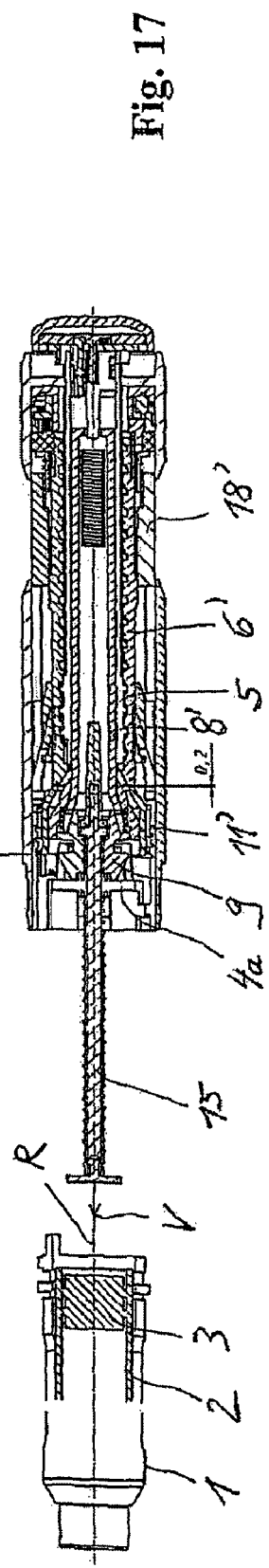

DEVICE FOR THE DOSED ADMINISTRATION OF A FLUID PRODUCT COMPRISING A TORSION SPRING DRIVE

CROSS-REFERENCE TO RELATED APPLICATIONS

This application is a continuation of International Application No. PCT/CH2005/000712, filed Nov. 30, 2005, which claims priority to German Application No. DE 10 2004 063 644.3, filed on Dec. 31, 2004, the contents of both of which are incorporated in their entirety herein by reference.

BACKGROUND

The present invention relates to devices for dispensing, delivering, injecting, infusing or administering substances, and to methods of making and using such devices. More particularly, it relates to a device for administering a fluid product in doses, comprising a torsion spring drive. In some embodiments, the device or apparatus of the present invention may be an injection apparatus, e.g., an injection pen.

Injection apparatus or devices are known from diabetes therapy, administering growth hormones or osteoporosis preparations. Such apparatus should guarantee that the correct dosage is administered, yet be simple and convenient to operate. These requirements are particularly important when a user administers the relevant product him/herself.

Injection apparatus, such as one known for from WO 01/10484, comprise a conveying means, a dosing means and a drive means. The user applies the drive force required for administering the product him/herself, by charging the drive means with the drive force. The drive means is coupled to the conveying means such that the drive force introduced is converted into a conveying action of the conveying means.

An injection apparatus follows from WO 02/053214 A1 which uses a drive spring to generate the drive force, wherein said drive spring is tensed for setting the dosage and releases the stored energy during delivery. A spring which is wound around an axis in a spiral serves as the drive spring, the windings of which lie adjacently along the axis. Due to the drive spring, the user no longer has to apply the drive force and can thus better concentrate on the other manual operations required for administering. On the other hand, the injection apparatus can only administer a fixedly predetermined dosage.

SUMMARY

It is an object of the present invention to provide a device for administering a dose or dosage of fluid product which is simple and secure to operate, and enables the dosage to be administered to be flexibly set.

In one embodiment, the present invention comprises a device for administering a fluid product comprising a housing, a conveying device for the product, a coupling element provided for the drive of the conveying device and which can be rotated about a rotational axis, a first blocking element connected in a rotationally secure manner to the coupling element, a second blocking element detachably engageable with the first blocking element thereby preventing a rotational movement thereof in the drive direction and enabling said rotational movement to take place in the counter dosing direction, a torsion spring connected to the coupling element such that it is stressed by the rotational movement when the blocking elements are engaged in a blocked position and drives the coupling element in a rotary manner after the blocking position is released, and a release element coupled to at least one of the blocking elements such that a release movement of the release element displaces at least one of the blocking elements from the blocked position, the release element also forming a dosing element used to control a product dose.

In one embodiment, the present invention relates to a device for administering a fluid product which comprises a casing comprising a reservoir. The reservoir can itself form a container for the product or can accommodate a container for the product, for an ampoule. The device also includes a conveying means, the conveying action of which conveys product from the reservoir or a container accommodated in it. The device also includes a coupler member which can be rotationally moved about a rotational axis for driving the conveying means, a first blocking member which is connected, such that it is secured against rotating, to the coupler member, and a second blocking member which, in a releasable blocking engagement with the first blocking member, prevents a rotational movement of the first blocking member and therefore also of the coupler member in a drive direction and allows a rotational movement of the first blocking member and therefore also of the coupler member in an opposite dosing direction. In some embodiments, the device comprises a torsion spring and a triggering element coupled to at least one of the blocking members such that a triggering movement of the triggering element moves the at least one of the blocking members out of the blocking engagement. The torsion spring is connected to the coupler member such that when the blocking members are in blocking engagement, the torsion spring is tensed by a rotational movement of the coupler member in the dosing direction, the spring energy thus stored is released after the blocking engagement is released, and the coupler member is rotationally driven in the drive direction.

In accordance with the present invention, the triggering element not only serves to release the blocking engagement and consequently trigger the torsion spring, but also—in a double function—forms a dosing member for setting the dosage. The triggering element is correspondingly coupled to the torsion spring such that when the blocking members are in blocking engagement, the torsion spring is tensed by a dosing movement of the triggering element. For the triggering movement, the triggering element can be moved translationally along the rotational axis. For the dosing movement, the triggering element can be moved rotationally about the rotational axis. For simple handling when administering the product, it is advantageous if the triggering element is arranged in a proximal end region of the injection apparatus. For the triggering function, the trigger element may be a push button which, when administering, is operated in the direction of the administering location or injection site.

In some preferred embodiments, a dosage can also be corrected by the triggering element. For the correcting function, the triggering element is coupled to at least one of the blocking members, such that a retracting movement of the triggering element moves the relevant blocking member out of the blocking engagement. For correcting the dosage, the torsion spring is decoupled from the conveying means, such that product cannot be inadvertently delivered. It can be decoupled by the retracting movement. In some preferred embodiments, however, a coupler for driving the conveying means connects the torsion spring to it. In a resting state which the apparatus is always in when the triggering element is unstressed, the coupler is advantageously released, while the triggering element is still coupled to the coupler member even during the retracting movement and in its fully retracted state, such that the user can prevent the coupler member from rotating in the drive direction by holding the triggering element. Operational errors while correcting the dosage could at most lead to the dosage set being reduced past the desired level, which however can be corrected again without any further consequences by letting go of the triggering element and re-dosing. In some preferred embodiments, the retracting movement is counter to the triggering movement.

In embodiments in which a holding means, holder or holding fixture holds the coupler in a released, i.e. retracted, state when the blocking members are in blocking engagement, such that the conveying means and the coupler member are decoupled from each other, the coupler member and the conveying means are advantageously coupled to each other by the triggering movement of the triggering element. In its triggering movement, the triggering element thus not only releases the blocking engagement of the blocking members but additionally establishes a coupler engagement in the course of the same movement, via which the torsion spring drives the conveying means after the blocking engagement of the blocking members is released. For this purpose, the triggering movement is advantageously divided into functional phases which progress in succession and which could be performed continuously. Expediently, the coupler member is coupled to the conveying means and, if the coupling already exists, the blocking engagement is released in a subsequent phase. The coupler engagement is embodied to be long enough for overlapping in the direction of the coupler movement.

In one development of the present invention, the triggering element not only performs the double function in accordance with the invention, but in a third function triggers the injection of an injection needle if, as in some preferred embodiments, the apparatus is equipped with an injection needle and not formed as a pressure injector. A needle protection, protector or cover which is connected to the casing such that it elastically gives is coupled to the triggering element by a resisting element via the casing, such that the needle protection can be moved up to and against the resisting element in a first phase of the injection process, and in the position then assumed by the needle protection, the triggering element acts via a coupling mechanism on at least one of the needle protection and the resisting element, such that a positive-lock or frictional-lock contact between the two, which prevents a further movement of the needle protection in the proximal direction, is released. The coupling mechanism for the injection process controlled in this way and the coupling between the triggering element and the at least one of the blocking members for releasing the blocking engagement are configured such that during the triggering movement, the triggering element first releases the needle protection, such that the injection needle can penetrate, and in the subsequent course of the triggering movement the blocking engagement of the blocking members is released.

In preferred embodiments in which the device of the present invention includes a coupler which can be extended and retracted, the coupler couples the coupler member to the conveying means in a coupler engagement, i.e. in the extended state of the coupler, to transfer the drive force of the torsion spring for delivering the product onto the conveying means. In the retracted state, it decouples the conveying means from the coupler member, such that manipulations acting on the coupler member, such as for setting a dosage or correcting a dosage, cannot influence the conveying means. In such embodiments, the triggering movement of the triggering element again causes the coupler engagement to be established by a coupler movement of a coupler member, e.g., the coupler member cited above, or multiple coupler members, including the coupler member cited above. In some embodiments, the coupler member can always be coupled to the conveying means, though for the purposes of delivery it must first be released by performing the triggering movement.

The coupler consists of at least two coupler members, the above-described coupler member which forms the coupler input member and the other of which is coupled to the conveying means as a coupler output member. At least one of the coupler members, e.g., the coupler input member, can be moved into the coupler engagement, and at least one of the coupler members—not necessarily the same one—can be moved out of the coupler engagement.

In accordance with the present invention, in some embodiments, the device also includes a holding means, holder or holding fixture which holds the coupler members in a holding position, decoupled from each other. Correspondingly, at least one of the coupler members can be moved by a coupler movement from the holding position into the coupler engagement. In the holding position, the flow of forces between the coupler members is interrupted. In the coupler engagement, by contrast, the drive force of the drive member can be transferred onto the conveying means via the coupler members and causes a delivery movement of the conveying means.

The engaging elements of the relevant coupler members, which in the coupler engagement interlock with each other in a positive lock or, as applicable, are merely pressed against each other in a frictional lock, are retracted from each other in the holding position. The coupler members themselves can in fact contact each other, even in the holding position, but their engaging elements are not in contact in the holding position. In some preferred embodiments, the coupler members—which are in the coupler engagement in their coupled state—are completely retracted from each other in their decoupled state.

In some preferred embodiments, the holding means is or includes a restoring member which acts counter to the coupler movement with an elastic restoring force. Instead of holding the coupler in its decoupled state in the holding position by an elastic force, as is preferred in some embodiments, the holding means could also act in a positive lock, by fixing the at least one coupler member performing the coupler movement on the casing or on a structure which is fixedly connected to it at least with respect to the coupler movement, in a releasable positive lock. The torsion spring itself can form the restoring member, or a dedicated restoring member may be provided specifically for the holding function.

In the coupled state of the coupler, the coupler input member and the coupler output member can be directly in coupler engagement with each other. In one development, however, the coupler includes a coupler intermediate member, via which the coupler input member is coupled to the coupler output member in the coupler engagement. In some preferred embodiments, the coupler engagement is established between the coupler input member and the coupler intermediate member. The coupler intermediate member is in an engagement—in which the drive force can be transferred—with the coupler output member, even in the holding position of the coupler members, i.e. in the decoupled state. Advantageously, it can be moved relative to the coupler output member in said engagement, in and counter to the direction of the coupler movement.

In a further development, the coupler output member is fixed on the casing in the holding position of the coupler members, such that it cannot perform any movement which would cause a delivery movement of the conveying means. The coupler output member has to be deliberately released, directly connected with delivering the product. It is advantageous if the fixation on the casing is released by performing the coupler movement. In some preferred embodiments, the coupler engagement is established in a first phase during a path portion traveled during the coupler movement, and the fixation on the casing is released in a subsequent, second phase, advantageously against the above-described elastic restoring force of the holding means. Advantageously, the coupler output member is fixed on the casing in the holding position of the coupler members via the coupler intermediate member. The blocking engagement which exists for this purpose between the coupler intermediate member and the casing or a structure connected to it is expediently released by performing the coupler movement. It is advantageous if the coupler intermediate member can be moved in the direction of the coupler movement, out of the blocking engagement, since such a mobility allows the coupler intermediate member to be slaved, for pressed out of the blocking engagement, during the coupler movement. The blocking engagement can be a positive-lock engagement and/or a frictional-lock engagement.

In a first variant, the restoring member acts on the coupler member via the coupler intermediate member and holds it in the holding position. In a second variant, the restoring member acts directly on the coupler member and is supported, for charging, on the casing or on a structure which is fixedly connected to the casing with respect to the coupler movement or on the coupler output member.

The coupler output member is in engagement with the conveying means, in some preferred embodiments, in a threaded engagement. In some embodiments they could be coupled indirectly to the conveying means via intermediate members to deliver the product. In a preferred threaded engagement, a rotational movement of the drive member is converted into a translational movement of a conveying member of the conveying means. The threaded engagement is advantageously not self-locking, such that the conveying member can be axially moved by a force exerted, in the direction of the threaded axis, on the conveying member which can be translationally moved in the threaded engagement.

In some preferred embodiments, the device of the present invention has a dosage display for displaying the product dosage set. The display can be an acoustic display, and/or a tactile display, and/or an optical display. The dosage display is coupled to the dosing member such that a movement which the dosing member performs when the product dosage is being set causes a change in the product dosage displayed. In the holding position of the coupler members, the dosing member and/or the dosage display is/are decoupled from the conveying means. The decoupling enables the dosage to be set and, as applicable, corrected in the decoupled state, without having a feedback effect on the conveying means.

In a preferred embodiment, the coupling between the dosage display and the torsion spring remains extant in the coupler engagement, such that as delivery progresses, a drive movement of the torsion spring, counter to the dosing movement, is progressively reset in the same way. If administering is impacted or prematurely aborted, whether deliberately or erroneously and unknowingly, the dosage display thus displays the remainder of the dosage set which has not yet been delivered. This can for be advantageous when the dosage set is larger than what is still available.

In the coupler engagement, the triggering element is advantageously decoupled from the torsion spring, such that during the drive movement of the torsion spring on the triggering element, no manipulations can be performed which would have a feedback effect on the torsion spring.

In some embodiments, the torsion spring can be a spiral spring. The spiral spring is wound around a rotational axis of the rotational movement, wherein at least one outer spring winding advantageously surrounds an inner spring winding. The spring exhibits a zero pitch with respect to the rotational axis all over. Using the spiral spring can save on axial length, as compared to the springs from the prior art, the windings of which are arranged axially next to each other. One of the two ends of the spiral spring, e.g., its radially inner end, is connected, such that it is secured against rotating, to the coupler input member. The other end, e.g., the radially outer end, is connected, such that it is secured against rotating, to the casing. The coupler input member advantageously forms a reel on which the spiral spring is wound. When setting the dosage, the coupler member is rotated about the rotational axis, which tenses the spiral spring.

In some preferred embodiments, the coupler movement is an axial stroke movement. If a piston and a piston rod form the conveying means, the coupler movement is performed in the advancing direction of the piston and the piston rod. The coupler members between which the coupler engagement is formed, can be provided with engaging elements which in the coupler engagement co-operate as grooves and springs which can be shifted axially with respect to each other or are formed as teeth or conical teeth, axially facing each other. Although a single tooth and a single tooth gap are in principle sufficient for the coupler engagement, in some preferred embodiments, at least one of the coupler members forming the coupler engagement is formed with teeth encircling the rotational axis. In some preferred embodiments, each of the two coupler members for the coupler engagement circumferentially comprises teeth or a textured region. The same applies to engaging elements formed as grooves and springs or formed otherwise. Irrespective of the shape of the coupler areas, the coupler engagement is formed such that slip does not occur in the coupler engagement.

In one development of the present invention, in which the casing includes at least two casing parts which can be detached from each other, one of which forms the reservoir and the other of which mounts the torsion spring, the coupler member and the blocking members, the injection apparatus is equipped with a decoupling mechanism. The decoupling mechanism is coupled to at least one of the blocking members, such that when the casing parts are detached by the relative movement to be performed between the casing parts for this purpose, the blocking engagement is released, such that the torsion spring moves the coupler member into a zero dosage position if it has not already assumed the zero dosage position. The decoupling mechanism includes a decoupling member which is moved into a decoupling position by the relative movement to be performed when detaching the casing parts. The decoupling member is coupled to said at least one of the blocking members, such that this decoupling movement moves the relevant blocking member out of the blocking engagement. The decoupling member acts on the coupler member and moves it into a decoupling position as well, and the coupler member moves the relevant blocking member out of the blocking engagement, e.g., via a slaving engagement. In the decoupling position, the decoupling member advantageously decouples the coupler member from the conveying means.

In another development of the present invention, the first blocking member which is connected, such that it is secured against rotating, to the coupler member fulfils another function in addition to the blocking function, namely that of limiting the rotational movement of the coupler member in the drive direction. In this other function, it determines the zero dosage position of the coupler member. For this purpose, the first blocking member is provided with a thread around the rotational axis, and at least one rotational stopper for engaging a stopping member is formed at one end of the thread. The casing, or a structure connected to it such that it cannot be moved, guides the stopping member—such that it is secured against rotating—parallel to the rotational axis, such that the stopping member is moved axially back and forth when setting the dosage and during delivery, and stops the rotational movement of the coupler member when it abuts against the rotational stopper.

The first blocking member can be connected to the coupler member such that it cannot be axially moved. In some preferred embodiments, the coupler member and the first blocking member can be moved axially relative to each other, wherein the first blocking member is pressed in an axial direction into the blocking engagement by an elastic restoring member, until it maximally abuts against the coupler member. This restoring member can advantageously also be the restoring member or a restoring member of the holding means.

The present invention encompasses embodiments of injection apparatus comprising a torsion spring drive. It also encompasses embodiments wherein a triggering element, which releases a blocking engagement, itself forms a blocking member and embodiments, wherein the blocking engagement is not released by the dosing movement of the triggering element, for because the dosing movement is an axial movement.

BRIEF DESCRIPTION OF THE DRAWINGS

FIG. 1 shows an embodiment of an injection apparatus in accordance with the present invention, in a perspective view;

FIG. 2 shows the injection apparatus of FIG. 1 with the coupler open, in a longitudinal section;

FIG. 3 shows the injection apparatus of FIG. 1 with the coupler closed;

FIG. 6 shows the injection apparatus of FIG. 1 after a dosage has been set;

FIG. 7 shows the injection apparatus of FIG. 1 after a reservoir has been emptied;

FIG. 8 shows a decoupling member and a casing part of the injection apparatus of FIG. 1;

FIG. 9 shows a distal portion of the injection apparatus of FIG. 1 with the casing parts connected;

FIG. 10 shows the distal portion while the casing parts are being detached;

FIG. 15 shows the injection apparatus of FIG. 11, after a dosage has been set;

FIG. 16 shows the injection apparatus of FIG. 11, after the reservoir has been emptied;

FIG. 17 shows the injection apparatus of FIG. 11, with the casing parts detached from each other;

DETAILED DESCRIPTION

Figure 4:
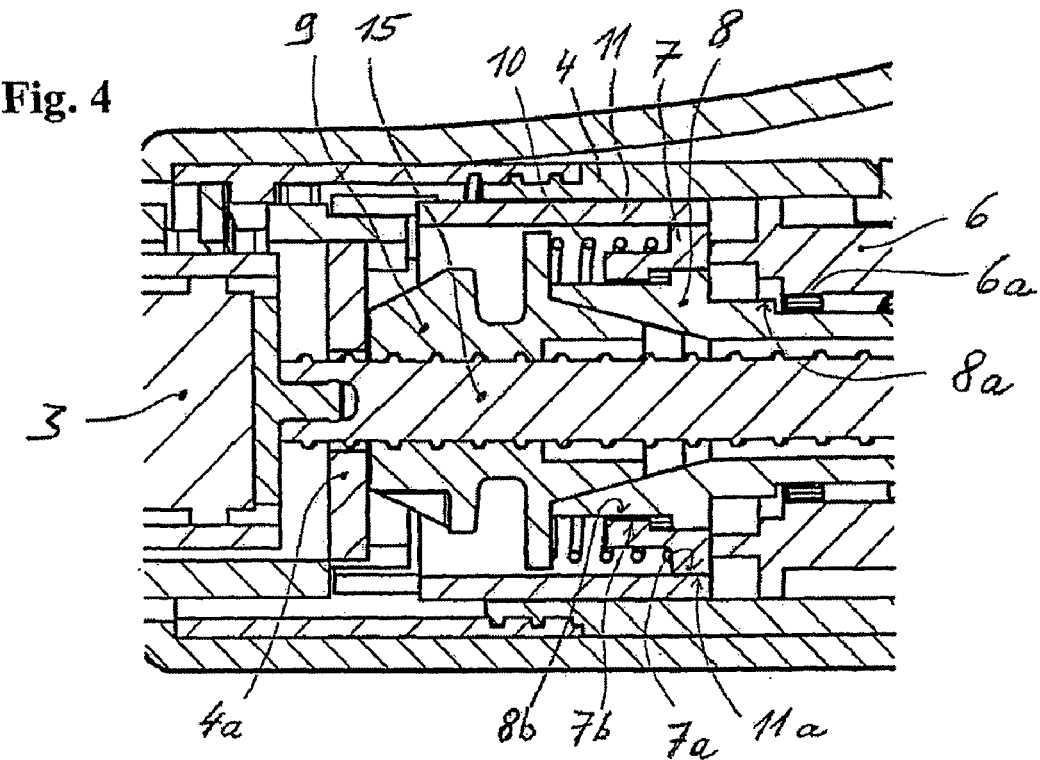
FIG. 4 shows a detail from FIG. 2.

With regard to fastening, mounting, attaching or connecting components of the present invention, unless specifically described as otherwise, conventional mechanical fasteners and methods may be used. Other appropriate fastening or attachment methods include adhesives, welding and soldering, the latter particularly with regard to the electrical system of the invention, if any. In embodiments with electrical features or components, suitable electrical components and circuitry, wires, wireless components, chips, boards, microprocessors, inputs, outputs, displays, control components, etc. may be used. Generally, unless otherwise indicated, the materials for making the invention and/or its components may be selected from appropriate materials such as metal, metallic alloys, ceramics, plastics, etc.

FIG. 1 shows an injection apparatus of one embodiment of the present invention. The injection apparatus comprises a first casing part 1 and a second casing part 4 detachably connected to each other. In one embodiment, the casing parts 1 and 4 are screwed to each other. The injection apparatus is formed as a slim injection pen. The casing part 1 serves to accommodate a container 2 filled with a fluid product and in this sense forms a reservoir, and the casing part 4 serves as a bearer for a dosing and drive means, a dosing member 18 of which can be seen. The casing part 4 is breached in the region of the dosing member 18, such that a user has direct access to the dosing member 18. The dosing member 18 is mounted such that it can be rotated about a central longitudinal axis of the apparatus, and formed as a sleeve which is ribbed on its outer circumference so as to be user-friendly. A dosage display 20 can also be seen, which is laterally placed through a breach in the shell of the casing part 4.

FIG. 2 shows the injection apparatus of the first embodiment in a longitudinal section. The container 2 is accommodated in the casing part 1. In the container 2, a piston 3 is accommodated such that it can be moved in an advancing direction V. The piston 3 seals the container 2, fluid-proof, at its proximal end. Advancing the piston 3 in the advancing direction V displaces and delivers product through an outlet of the container 2, through an injection needle protruding into the outlet and fastened to the distal end of the casing part 1 by means of a needle holder. The container 2 is formed in the manner of conventional ampoules. The casing part 1 directly forms a container holder; in the embodiment shown, an ampoule holder. The proximal end of the casing part 1 protrudes into the casing part 4 and is screwed to the casing part 4.

The casing part 4 accommodates a piston rod 15 and the dosing and drive means which is formed as a dosing and drive mechanism. In a dosing and drive line, the dosing and drive means includes a drive member 5 and a coupler (which may comprise components 6-11) which in a coupled state, i.e. in a coupler engagement, couples the drive member 5 to the piston rod 15. The piston rod 15, together with the piston 3, forms a conveying means. In the coupled state, coupler members 6-10 transfer a drive force exerted on the drive member 5 onto the piston rod 15. No coupler engagement exists in FIG. 2, such that the piston rod 15 is decoupled from the drive member 5. In this decoupled state, the user can set the product dosage to be administered, by a dosing movement of the dosing member 18; in the embodiment, a rotational movement.

The drive member 5 is sleeve-shaped. On its shell outer area, it comprises a thread about a threaded axis R pointing in the advancing direction V. Via this thread, the drive member 5 is in threaded engagement with a coupler input member 6. The coupler input member 6 is also sleeve-shaped and provided with a corresponding inner thread for the threaded engagement. The thread pitch in the threaded engagement is large enough that self-locking cannot occur. The dosing member 18 surrounds the coupler input member 6 and is connected to the coupler input member 6 such that it is secured against rotating and cannot be moved axially. The piston rod 15 protrudes into the drive member 5 and the coupler input member 6.

The piston rod 15 is provided with an outer thread over its axial length. Via the outer thread, it is in threaded engagement with a coupler output member 9 which is provided with a corresponding inner thread. These two threads also exhibit a thread pitch which prevents self-locking in the threaded engagement. In some embodiments, the thread pitch is less than the thread pitch in the threaded engagement between the drive member 5 and the coupler input member 6. A coupler sleeve 8 is connected to the coupler output member 9 such that it is secured against rotating and cannot be moved axially. The coupler sleeve 8 and the coupler output member 9 can be regarded as an integral component with respect to the movements between the drive member 5 and the piston rod 15; however, to accommodate an equalizing spring 17, they are embodied in two parts and fixedly connected to each other. The coupler output member 9 and the coupler sleeve 8 are mounted in the casing part 4 such that they can be rotated about the threaded axis R of the coupler output member 9 but cannot be moved axially. In the threaded engagement, the piston rod 15 protrudes through the coupler output member 9 and protrudes into the coupler sleeve 8. The equalising spring 17 is clamped between a proximal end of the coupler sleeve 8 and a proximal end of the piston rod 15 and acts on the piston rod 15 in the advancing direction V as a pressure spring. The equalizing spring 17 presses onto the piston rod 15 via a disc 15a which is supported such that it can be rotated on the piston rod 15 and forms a flange of a sleeve placed onto the piston rod 15.

The piston rod 15 is linearly guided in and counter to the advancing direction V in a linear guide 4a, such that it cannot be rotated relative to the casing part 1. The drive member 5 is also linearly guided relative to the casing part 4 such that it can be moved in and counter to the advancing direction V, for which purpose the casing part 4 directly forms a linear guide 4b.

The threaded axis of the piston rod 15 forms a main movement axis of the device. It forms a rotational axis R for the rotational drive movement of the coupler input member 6 and, via the coupler intermediate member 7, the coupler output member 9. It forms both threaded axes. It also forms the translational axis for the piston rod 15 and the drive member 5.

The coupler also includes a coupler intermediate member 7 and a restoring member 10 which is formed as a pressure spring and charges the coupler intermediate member 7 with an elasticity force acting counter to the advancing direction V. The restoring member 10 is clamped between the coupler output member 9 and the coupler intermediate member 7.

If no force acting in the advancing direction V is exerted on the drive member 5, the restoring member 10 ensures, via the coupler intermediate member 7, that the coupler engagement is released. This state is shown in FIG. 2. The coupler input member 6 is pressed in the advancing direction V until it abuts against the coupler intermediate member 7, and is pressed into a proximal end position by the restoring member 10 via the coupler intermediate member 7. By the coupler intermediate member, the restoring member 10 holds the coupler input member 6 in a holding position relative to the coupler output member 9 and the coupler sleeve 8 fastened to it. The restoring member 10 and the coupler intermediate member 7 thus form a holding means, acting in a non-positive lock, for the coupler input member 6.

FIG. 3 shows the injection apparatus in a coupled state. A coupler engagement exists between the coupler input member 6 and the coupler sleeve 8. For the coupler engagement, the coupler input member 6 and the coupler sleeve 8 form engaging elements which, in the coupler engagement, establish a rotationally secured connection between the two members 6 and 8 about the threaded axis R pointing in the advancing direction V. The engaging elements co-operate as grooves and springs or teeth which are formed parallel to the advancing direction V and evenly distributed about the threaded axis R.

Figure 5:
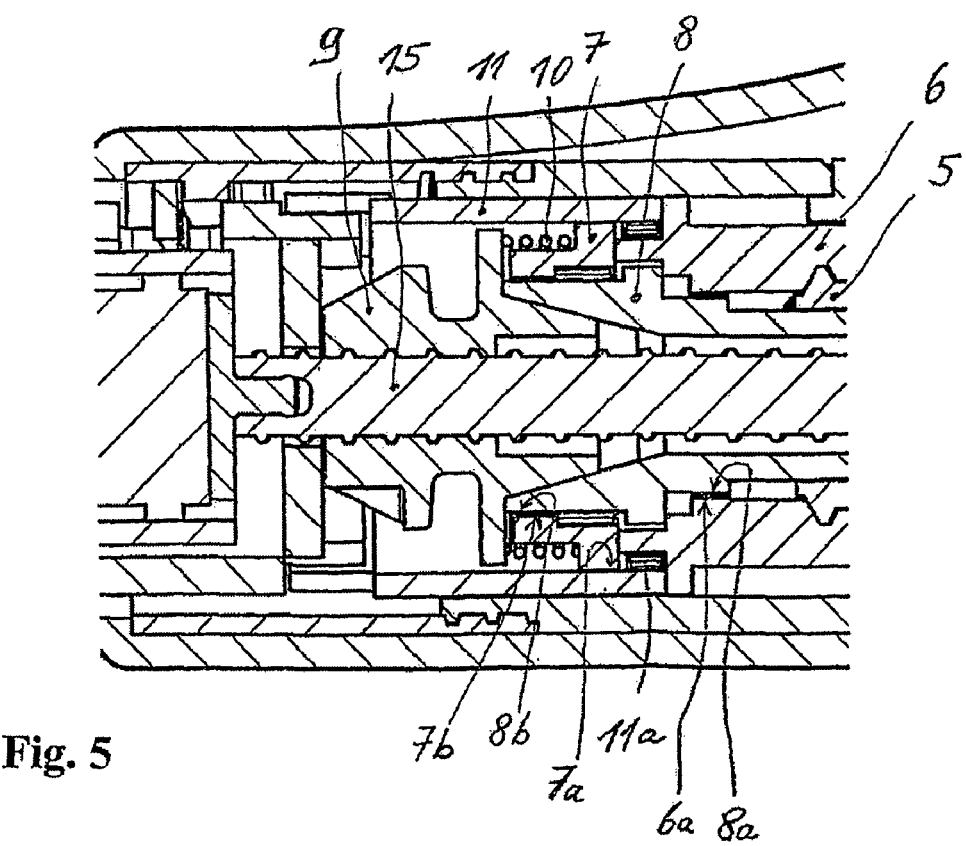
FIG. 5 shows a detail from FIG. 3.

FIGS. 4 and 5 show the region of the coupler engagement in detail. FIG. 4 shows the apparatus in the decoupled state and FIG. 5 shows the apparatus in the coupled state. FIG. 4 thus corresponds to FIG. 2, and FIG. 5 thus corresponds to FIG. 3.

In the decoupled state, the coupler input member 6 is retracted from the coupler sleeve 8 counter to the advancing direction V, such that the coupler input member 6 can be freely rotated relative to the coupler sleeve 8 and therefore the coupler output member 9 fixedly connected to it. The coupler output member 9 is simultaneously connected, such that it cannot be rotated, to the casing part 4 via the coupler sleeve 8, the coupler intermediate member 7 and a decoupling member 11. For this rotationally secure coupling, the coupler intermediate member 7 is provided with engaging elements 7b on an inner area radially facing the coupler sleeve 8, and the coupler sleeve 8 is provided with corresponding engaging elements 8b. For the rotationally secured engagement with the decoupling member 11, the coupler intermediate member 7 is provided with engaging elements 7a on an outer circumferential area, and the decoupling member 11 is provided with radially facing engaging elements 11a on a shell inner area which, in the decoupled state, interlock with each other—like the engaging elements 7b and 8b—in the manner of grooves and springs or teeth parallel to the advancing direction V. The coupler intermediate member 7, in its rotationally secured engagement with the coupler sleeve 8 and its rotationally secured engagement with the decoupling member 11, can be moved axially in and counter to the advancing direction V, wherein the engagement with the decoupling member 11 is released when it moves in the advancing direction V.

If the drive member 5 is operated by exerting a pressure force on a triggering element 16 in the advancing direction V, the drive member 5 and the coupler input member 6 together complete an axial coupler stroke of length X. In this drive stroke movement or coupler movement, the coupler input member 6 pushes the coupler intermediate member 7 in the advancing direction V, against the restoring elasticity force of the restoring member 10. In the course of the stroke movement, the engaging elements 6a and 8a pass into engagement with each other, while the coupler intermediate member 7 simultaneously moves relative to the decoupling member 11 until it passes out of the rotationally secured engagement with the decoupling member 11. The coupler intermediate member 7 remains in the rotationally secured engagement with the coupler sleeve 8. The coupler movement is limited by a stopper of the triggering element 16 on the coupler sleeve 8; in this exemplary embodiment, on its proximal facing area (FIG. 3).

FIG. 5 shows the injection apparatus in the coupled state. The engaging elements 6a and 8a are axially superimposed, such that the coupler engagement is established as a rotationally secured engagement between the coupler input member 6 and the coupler sleeve 8. The engagement between the coupler intermediate member 7 and the decoupling member 11 is not released until the coupler engagement is securely established.

For setting the dosage, the user rotates the dosing member 18, which locks in easily releasable locking positions. The dosing member 18 is connected to the coupler input member 6 such that it is secured against rotating and also cannot be moved axially, such that the latter rotates with it. The drive member 5 guided linearly in and counter to the advancing direction V at 4b is moved, by the dosing movement of the coupler input member 6, in the proximal direction and then protrudes out of the casing part 4. The axial dosing path of the drive member 5 follows from the rotational angle by which the dosing member 18 is rotated and the thread pitch in the threaded engagement between the drive member 5 and the coupler input member 6 which abuts against the coupler intermediate member 7 in the advancing direction V and against the casing part 4 counter to the advancing direction V.

FIG. 6 shows the injection apparatus with the container 2 still completely filled, after a first dosage has been set. In this state, the user penetrates the skin with the injection needle, for a subcutaneous injection. Once the injection needle has been placed, the user operates the drive member 5 by pressing it in the advancing direction V, into the casing part 4. In the first portion of the drive movement, coupler movement or coupler stroke X, the drive member 5 slaves the coupler input member 6, against the elastic restoring force of the restoring member 10, until the coupler engagement with the coupler sleeve 8 is established and the rotationally secured engagement between the coupler intermediate member 7 and the decoupling member 11 is released. As soon as the coupler sleeve 8 and together with it the coupler output member 9 can freely rotate about the common threaded axis R, the coupler stroke X is complete and a delivery stroke follows as the second portion of the drive movement. During the delivery stroke, the drive member 5 is pressed further in the advancing direction V. Since the coupler input member 6 cannot perform any further movement in the advancing direction V once it abuts axially against the coupler intermediate member 7, it rotates—in the threaded engagement with the drive member 5 which is guided such that it is secured against rotating—about the common threaded axis R. When rotated in the coupler engagement, the coupler input member 6 slaves the coupler sleeve 8, which slaves the coupler output member 9. The coupler sleeve 8 is held in the casing part 4, together with the coupler output member 9, such that it cannot be moved axially. The rotational movement of the coupler output member 9 advances the piston rod 15, via the threaded engagement with the piston rod 15 and its rotationally secured linear guide at 4a, and thus causes the delivery movement of the piston rod 15 and together with it the piston 3. As soon as the injection button 16 passes into abutting contact against the coupler sleeve 8 in the course of the drive and delivery movement (FIG. 3), the delivery process is complete.

If the user takes the pressure off the triggering element 16, then the restoring member 10 moves the coupler input member 6, via the coupler intermediate member 7, back to the holding position retracted out of the coupler engagement, as shown in FIGS. 2 and 4. The coupler input member 6 and together with it the drive member 5, the dosing member 18 and the dosage display 20, are decoupled from the coupler output member 9 and thus from the piston rod 15 by the retracting movement of the coupler input member 6. On the other hand, the piston rod 15 is again connected to the casing part 4, such that it is secured against rotating, via the returning coupler intermediate member 7 and decoupling member 11.

FIG. 7 shows the injection apparatus at the end of a final delivery which has emptied the container 2.

For exchanging the emptied container 2, the casing part 1 is detached from the casing part 4; in this exemplary embodiment, by a screwing movement. When the casing parts 1 and 4 are detached, the decoupling member 11 is automatically moved relative to the casing part 4, counter to the direction of the coupler movement of the coupler input member 6; in the embodiment, counter to the advancing direction V. The casing part 4 mounts the decoupling member 11 accordingly. The axial path which the decoupling member 11 thus travels relative to the casing part 4 is as long as the coupler stroke X, such that once the casing parts 1 and 4 have been detached, the decoupling member 11 lying axially opposite the coupler input member 6 blocks it, and the coupler input member 6 can no longer be moved in the advancing direction V, at least not into the coupler engagement with the coupler sleeve 8. Blocking the coupler input member 6 in the disengaged position prevents the coupler output member 9 from being able to pass into a rotationally secured connection with the casing part 4 and so prevent the piston rod 15 from retracting. In other words, it ensures that the piston rod 15 can be retracted into the casing part 4, without being blocked.

FIG. 8 shows the decoupling member 11 and the first casing part 1 in a perspective view. The decoupling member 11 is a sleeve part and comprises, in a distal portion, three engaging elements 12 protruding radially inwards and, in a proximal portion, a fixing element 13 protruding radially outwards.

FIG. 9 shows the casing part 1 and a connecting portion of the casing part 4, wherein the hidden decoupling member 11 is shown by a broken line. For its decoupling function, the decoupling member 11 is accommodated in the connecting portion of the casing part 4 such that it can be rotated and moved axially. Its relative mobility is determined by an axial guide 4e and a circumferential guide 4c, along which the fixing element 13 moves in succession when the casing part 1 is detached from the casing part 4. The circumferential guide 4c extends at a right angle to the axial guide 4e, in the circumferential direction about the screw axis. It is formed as a breach or cavity in the casing part 4.

The decoupling member 11 is in a guiding engagement with the casing part 1. For the guiding engagement, one guiding curve 1a per engaging element 12 is formed on a shell outer area of the casing part 1 and guides the engaging element 12 and thus the decoupling member 11 when the casing parts 1 and 4 are detached. Another guiding curve 1a, spaced in parallel, guides the decoupling member 11 accordingly, when the casing parts 1 and 4 are connected (FIG. 10). In a distal portion, the guiding curve 1a runs obliquely, i.e. at a pitch, with respect to the screw axis of the screw connection between the casing parts 1 and 4, such that in the relative rotation between the casing parts 1 and 4, required for detaching them, the engaging element 12 performs an axial movement of the decoupling member 11 relative to the casing part 4 counter to the advancing direction V, sliding along the guiding curve 1a, until the fixing element 13 reaches the axial height of the circumferential guide 4c. The pitch measures about 45° and is constant. In principle, it can be selected from the entire range larger than 0° and smaller than 180° and, as applicable, can also be variable, as long as the relative movement required for detaching the casing parts 1 and 4—e.g, a screwing movement—causes a movement of the decoupling member counter to the coupler movement X to be performed by the coupler input member for coupling. A distal portion of the guiding curve 1*a* runs axially, such that when the casing parts 1 and 4 are screwed further apart, the fixing element 13 is moved along the circumferential guide 4*c*. In the course of this relative circumferential movement between the decoupling member 11 and the casing part 4, the fixing element 13 slides over a fixing element 4*d* in the region of the circumferential guide 4*c*. The fixing element 4*d* is formed as a cam on a strip portion of the casing part 4. The strip portion acts as a spiral spring which is fixedly clamped on both sides and elastically gives when the fixing element 13 moves over the fixing element 4*d*, to then spring back again into its initial position and form a releasable locking engagement for the decoupling member 11. In the locking position, the fixing element 13 abuts the fixing element 4*d* in one circumferential direction and in the other circumferential direction abuts a collar formed in the circumferential guide 4*c* and is thus fixed in both circumferential directions.

FIG. 10 shows the two casing parts 1 and 4 and the decoupling member 11, after its fixing element 13 has been moved behind the fixing element 4*d* of the casing part 4. The decoupling member 11 is in the releasable locking engagement with the casing part 4 via the fixing elements 4*d* and 13 and in this way is axially fixed on the casing part 4 such that it is secured against rotating. In the locking position shown in FIG. 10, the decoupling member 11 blocks the coupler input member 6 and thus ensures that the drive member 5 and the piston rod 15 are decoupled. As soon as the decoupling member 11 has reached the locking position, its engaging element 12 moves out of the guiding engagement with the guiding curve 1*a* when the casing parts 1 and 4 are screwed further apart. The guiding curve 1*a* is shaped accordingly.

When the casing parts 1 and 4 are screwed together again, they are centered with respect to the circumferential direction by co-operating centring elements, such that the engaging element 12 of the decoupling member 11 passes into engagement with the guiding curve 1*a* again. As soon as the guiding engagement has been established, further screwing together automatically moves the decoupling member 11 out of the locking engagement of the fixing elements 4*d* and 13 until it again assumes the same position relative to the casing part 4 as in FIG. 9 and FIGS. 2 to 7; this corresponds to the operational position of the decoupling member 11.

While or before screwing together, the piston rod 15 is simply retracted into the casing part 4, which—due to the released coupler engagement, causes a rotational movement of the coupler output member 9.

The dosage display 20 of the first embodiment is coupled to the drive member 5 via a display coupling member 21 and the coupler input member 6. The display coupling member 21 is connected to the coupler input member 6 such that it is secured against rotating, by being able to move on the coupler member 6 and relative to it in and counter to the direction of the coupler movement X, forming a ring in the embodiment. Conversely, the display coupling member 21 can be rotated with respect to the casing part 4 about the rotational axis R, but is held such that it cannot be moved axially relative to the casing part 4. The display coupling member 21 circumferentially comprises teeth, which in this exemplary embodiment are conical, via which it is in toothed engagement with a gear of the dosage display 20, to introduce the dosing movement and also the drive movement into the gear.

FIGS. 11-18 show another embodiment of an injection apparatus in accordance with the present invention. The injection apparatus of this embodiment exhibits some modifications as compared to the apparatus of the embodiment described above with regard to the coupling and decoupling of the drive member 5 and the piston rod 15. The drive member 5 and the piston rod 15 themselves, and how they co-operate in principle when coupling and decoupling, has however remained the same. Functionally identical components are provided with the same reference numbers. To indicate modifications, the relevant components are provided with the same reference numbers, but apostrophized.

Figure 11:
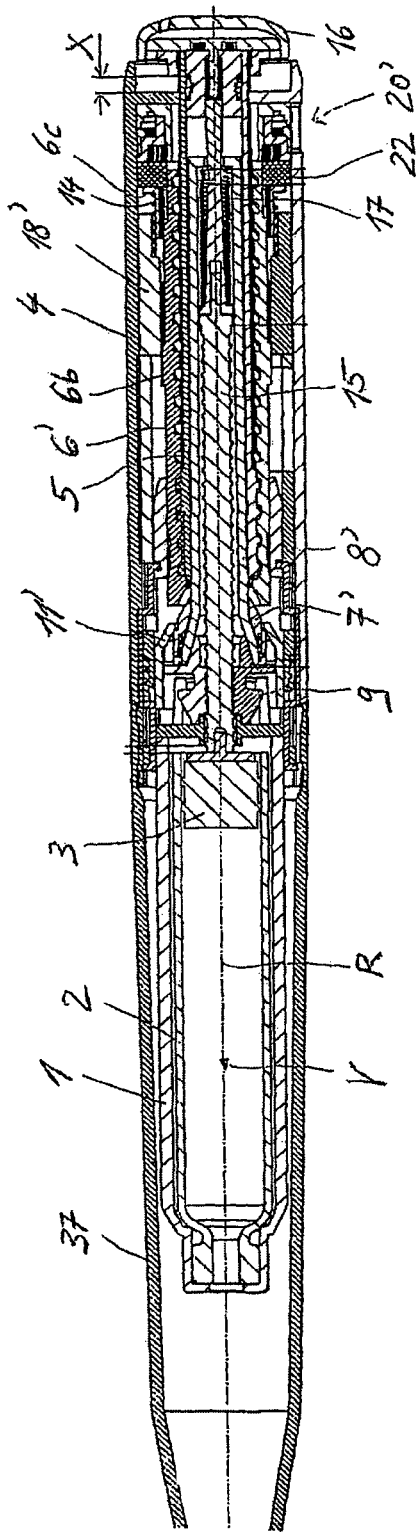
FIG. 11 shows another embodiment of an injection apparatus in accordance with the present invention, with the coupler open, in a longitudinal section.

FIG. 11 shows the injection apparatus in its resting state, in which the drive member 5 is decoupled from the piston rod 15. The first casing part 1 is covered by a protective cap 37 which is connected to the casing part 4 and removed for administering the product. Unlike the first embodiment, the coupler engagement is established and released between the modified coupler input member 6' and the modified coupler intermediate member 7'.

Figure 12:
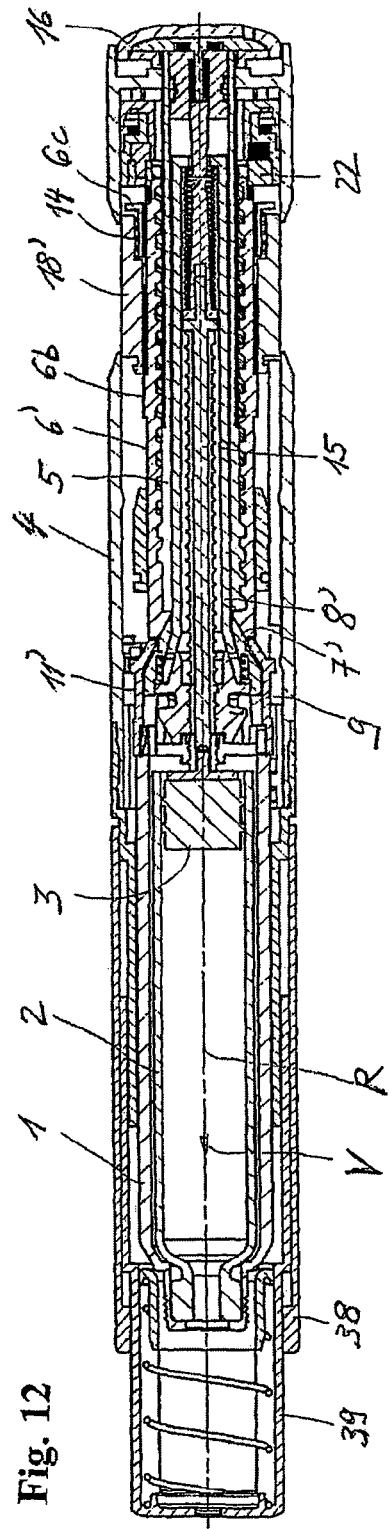
FIG. 12 shows the injection apparatus of FIG. 11 with the coupler closed, in a different longitudinal section.

FIG. 12 shows the injection apparatus of the second embodiment in its coupled state, which is established by charging the triggering element 16 and therefore the drive member 5 and the coupler input member 6' with a drive force acting in the advancing direction V. However, as in corresponding FIG. 3 of the first embodiment above, no dosage has yet been selected or only a small dosage of a few units for priming. The protective cap 37 has been replaced by a casing part 38 which is placed onto the casing part 4 and snapped onto it. The casing part 38 mounts a needle protection 39, e.g., in the form of a needle protecting sleeve, such that it can be elastically moved counter to the advancing direction V. When the injection needle (not shown) is injected, the needle protection 39 springs counter to the advancing direction V, into the casing part 38; in a reversal of this movement, the needle penetrates through a distal opening of the needle protection 39.

Figure 13:
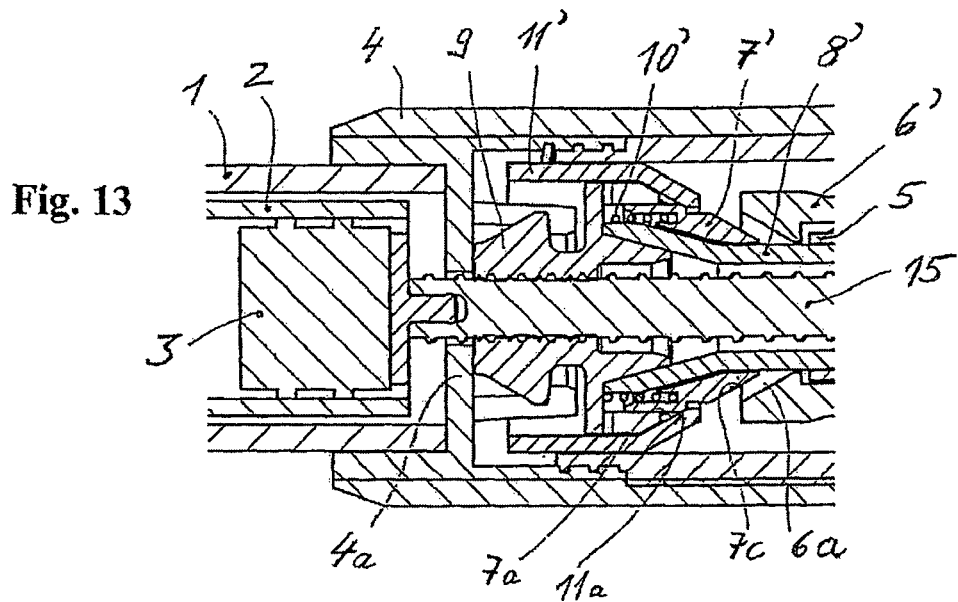
FIG. 13 shows a detail from FIG. 11.
Figure 14:
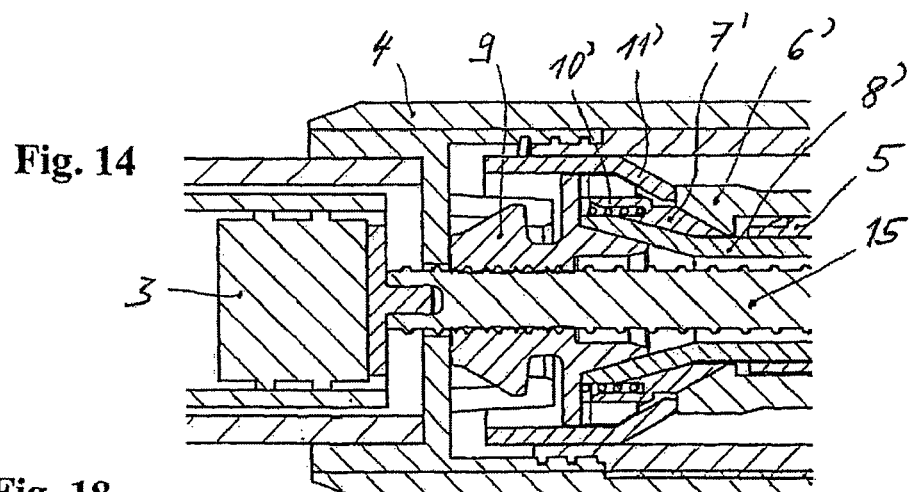
FIG. 14 shows a detail from FIG. 12.

FIGS. 13 and 14 show the region of the coupler engagement in detail, wherein FIG. 13 stands for the decoupled state and FIG. 14 stands for the coupled state. Unlike the first embodiment, the engaging elements 6*a* and 7*c* between which the coupler engagement is established exhibit an inclination with respect to the advancing direction V. In this embodiment, the engaging elements 6*a* and 7*c* are each formed in the manner of a ring of conical teeth encircling the threaded axis of the piston rod 15, wherein the coupler input member 6' forms its engaging elements 6*a* on its distal end as an inner cone, and the coupler intermediate member 7' forms the engaging elements 7*c* on its proximal end as an outer cone. The conical engaging areas are congruent to each other and lie directly opposite each other, axially facing, with the clear distance X. Instead of being conical, the coupler areas could also be shaped to be congruently convex/concave, or other suitable shapes.

Unlike the first embodiment, the coupler intermediate member 7' can be moved axially and is in engagement with the coupler output member 9, such that it is secured against rotating, in any axial position. It is again formed as a sleeve part and mounted on the coupler output member 9 such that it can be slid axially. For this purpose, it penetrates through the coupler sleeve 8' which is axially slit accordingly, which however is not visible in the figures. The rotationally secured connection is created in a positive lock via engaging elements formed as axially linear toothings. The restoring member 10', which is the same in its embodiment and installation but reduced with regard to its function, is tensed between the coupler output member 9 and the coupler intermediate member 7', as in the first embodiment, and charges the latter with an elasticity force, counter to the advancing direction V. In the decoupled state, in which the coupler input member 6' is retracted from the coupler intermediate member 7' counter to the advancing direction V, as shown in FIG. 13, the restoring member 10' presses the coupler intermediate member 7' into the rotationally secured engagement with the decoupling member 11'. The corresponding engaging elements are again indicated as 7a and 11a. The engaging elements 7a and 11a are also formed as conical toothed rings. The engagement between the coupler intermediate member 7' and the decoupling member 11' can alternatively be in a purely frictional lock. In this case, the engaging elements 7a and 11a comprise mutually facing congruent frictional areas; in some embodiments, these would be the mutually facing conical areas.

Another modification exists in the dosing member 18'. Unlike the dosing member 18 of the first embodiment, the dosing member 18' cannot be moved relative to the casing part 4 in the direction of the coupler movement X, the axial direction. Instead, the coupler input member 6' is again connected to the dosing member 18' such that it is secured against rotating, but such that it can be moved axially. The rotationally secured engagement between the coupler input member 6' and the dosing member 18' exists in the decoupled state of the drive member 5 and the piston rod 15 and is released in the course of the coupler stroke X, namely directly before the rotationally secured connection between the coupler output member 9 and the casing part 4 is released. For this engagement, the coupler input member 6' and the dosing member 18' are provided with engaging elements 6b and 18a which are formed on shell areas, radially facing each other, of the two members 6' and 18' in the manner of grooves and springs. With respect to the rotationally secured connection between the coupler input member 6' and the dosing member 18', reference may also be made to FIGS. 11 and 12. The rotationally secured connection exists in the decoupled state shown in FIG. 11, and is released in the coupled state shown in FIG. 12.

Another difference with respect to the first embodiment exists with regard to the holding means. In the second embodiment, the restoring member 10' has no effect which separates the coupler members 6' and 9 from each other. The holding means of the second embodiment includes a restoring member 14, a supporting structure 6c and the dosing member 18'. The restoring member 14 charges the coupler input member 6', via the supporting structure 6c, with an elastic restoring force which counteracts the coupler movement X of the coupler input member 6'. In the direction of the coupler movement X, which in the exemplary embodiments coincides with the advancing direction V, the restoring member 14 is supported on the dosing member 18' which forms a supporting collar for this purpose. The supporting structure 6c is connected to the coupler input member 6' such that it cannot be moved in or counter to the direction of the coupler movement X. It is formed as a short sleeve with an outer flange on which the restoring member 14 is supported. Counter to the direction of the coupler movement X, the supporting structure 6c abuts with respect to the casing part 4. The coupler movement X moves the coupler input member 6', against the elastic restoring force of the restoring member 14, into the coupler engagement with the coupler intermediate member 7'. As in the first embodiment, the restoring member 14 is formed as a pressure spring charged with a pressure force in the direction of the coupler movement X.

The mode of operation of the modified coupler (which may be thought of as comprising components 6'-11' and 14') is the same as the coupler of the first embodiment. Thus, in the decoupled state, the coupler output member 9 is connected, such that it is secured against rotating, to the casing part 4 via the coupler sleeve 8', the coupler intermediate member 7' and the decoupling member 11'. Operating the injection button 16 and consequently performing the coupler stroke X (FIG. 11) establishes the coupler engagement, in the second embodiment between the coupler input member 6' and the coupler intermediate member 7'. In the first phase of the coupler stroke X, the engaging elements 6a and 7c interlock with each other, such that the coupler input member 6' is connected, such that it is secured against rotating, to the coupler output member 9 via the coupler intermediate member 7' and the coupler sleeve 8'. Only once the rotationally secured engagement has been established is the coupler intermediate member 7' moved out of engagement with the decoupling member 11' by the coupler input member 6' pressing in the advancing direction V, such that the coupler output member 9 can freely rotate about the threaded axis R formed with the piston rod 15 and the coupler engagement is completely established.

FIG. 14 shows the injection apparatus in its coupled state, i.e. in the coupler engagement. FIGS. 15 and 16 generally correspond to FIGS. 6 and 7 of the first embodiment, such that reference can be made to these.

FIG. 17 shows the injection apparatus of the second embodiment while the reservoir 2 is being exchanged. Once the reservoir 2 has been emptied, as shown in FIG. 16, the casing part 1 is detached from the casing part 4, which moves the decoupling member 11' into the decoupling position. This function fully corresponds to that of the decoupling member 11 of the first embodiment, such that reference can be made to the explanations in that embodiment and to FIGS. 8-10.

In the state shown in FIG. 17, the casing part 1 is already accommodating the new reservoir 2. To connect the casing part 1 to the casing part 4, the casing part 1 can be moved towards the casing part 4 using the piston 3 which proximally seals the reservoir 2. The piston rod 15 which freely protrudes out of the casing part 4 is moved back by the pressing piston 3 in the threaded engagement with the coupler output member 9 which can be freely rotated but is axially fixed. Due to the rotationally secured linear guide 4a, which in the second embodiment is formed by a coupler receptacle which is inserted into the casing part 4 such that it is secured against rotating, the piston rod 15 completes an axial linear movement when retracted, while the coupler output member 9 freely rotates, together with the coupler sleeve 8', about the common threaded axis. Instead of moving the piston rod 15 back, pressing against the piston 3, the piston rod 15 can also be moved back beforehand by pressing directly on its plunger.

Figure 18:
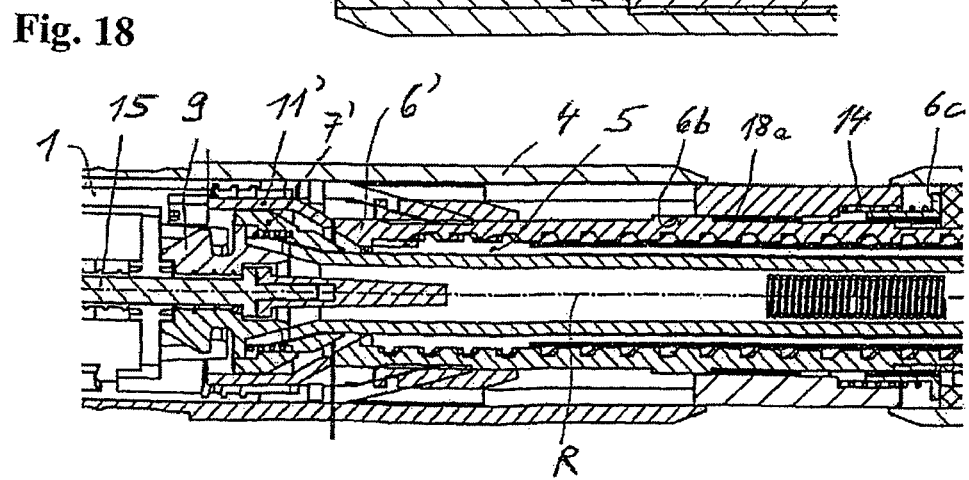
FIG. 18 shows a detail from FIG. 17.

FIG. 18 shows the coupler region, with the decoupling member 11' situated in the decoupling position, in detail. The function of the decoupling member 11' corresponds to that of the first embodiment, namely blocking the coupler input member 6' in the retracted axial position.

The dosing movement and the drive movement are also introduced into a gear of the dosage display 20' via the coupler input member 6' and a display coupling member 22 in the second embodiment. The display coupling member 22 is also connected to the coupler input member 6', such that it is secured against rotating, and cannot be moved relative to the casing part 4 in and counter to the direction of the coupler movement X.

FIGS. 19-24 show a third exemplary embodiment of an injection apparatus in accordance with the present invention, in which during administering, the drive force for delivering the product is not applied manually but rather by a drive member 25 formed as a drive spring. The drive member 25 is tensed by setting the dosage to be administered. The spring energy absorbed when setting the dosage is released when the apparatus is triggered and converted into advancing the piston rod 15.

Figure 19:
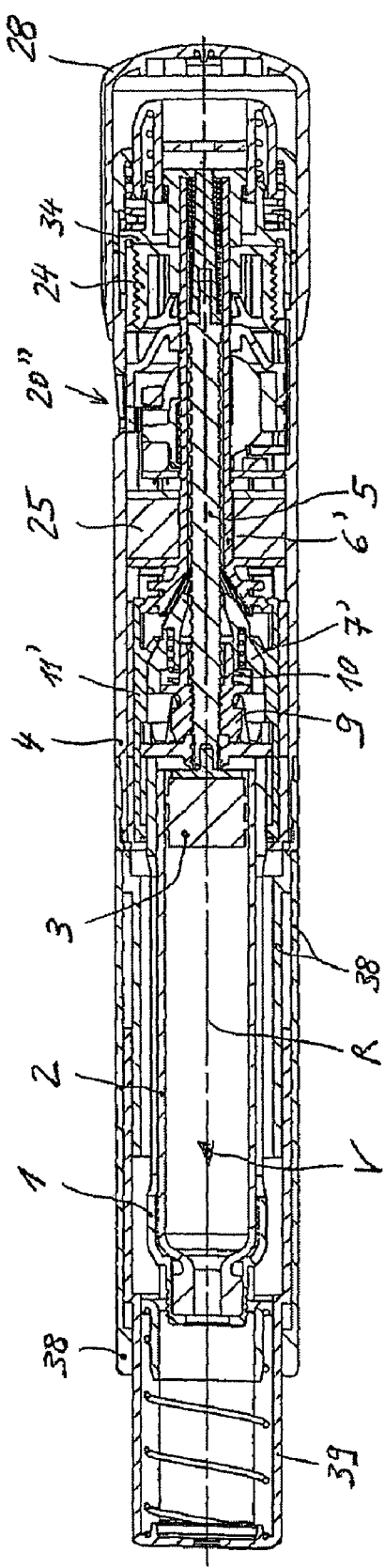
FIG. 19 shows another embodiment of an injection apparatus or device in accordance with the present invention.

FIG. 19 shows the injection apparatus of the third embodiment, complete with the assembled casing part 38 and the needle protection 39 accommodated in it such that it can be slid counter to the advancing direction V, against the force of a restoring spring.

Figure 20:
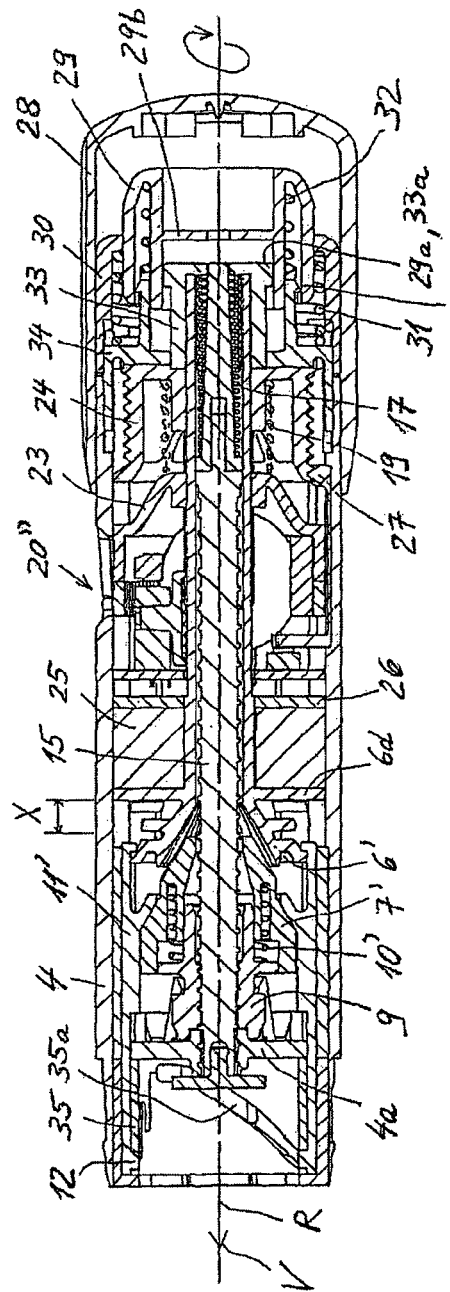
FIG. 20 shows a proximal part of the injection apparatus of FIG. 19, with the coupler open.
Figure 21:
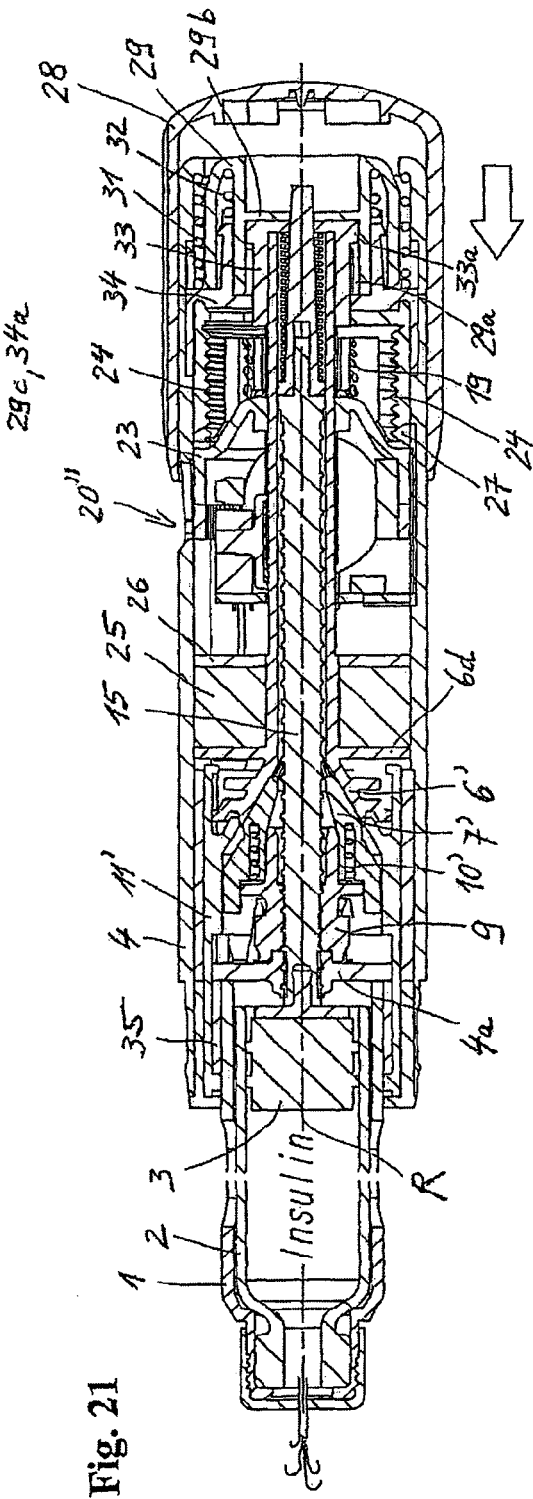
FIG. 21 shows the injection apparatus of FIG. 19, with the coupler closed.

FIGS. 20 and 21 show the casing part 4 with the components of the injection apparatus accommodated in it; FIG. 20 in a resting state, comparable to the preceding embodiments, in which the dosage can be set, and FIG. 21 in the coupler engagement. Unless stated differently below, reference is made in particular to FIGS. 20 and 21.

The drive member 25 is a spiral spring acting as a torsion spring, comprising spring windings which encircle the threaded axis R of the threaded engagement between the coupler output member 9 and the piston rod 15. The spring windings are arranged one over the other, radially with respect to the threaded axis R; they exhibit a zero pitch with respect to the threaded axis. An inner end of the spring windings is fastened to the coupler input member 6', and an outer end is fastened to a supporting structure 26 which is connected to the casing part 4 such that it can be moved in the direction of the coupler movement X but is secured against rotating. On the other hand, the supporting structure 26 is connected to the coupler input member 6' such that it cannot be moved in and counter to the direction of the coupler movement X. The coupler input member 6' can be rotated about the threaded axis R relative to the supporting structure 26. Another supporting structure 6d is connected to the coupler input member 6' such that it cannot be moved in and counter to the direction of the coupler movement X; in the embodiment, the coupler input member 6' and the supporting structure 6d are formed integrally. The drive member 25 is axially enclosed by the supporting structures 6d and 26.

The functionality of the coupler corresponds to that of the second embodiment, such that the same reference signs are used for the coupler members 6'-10' and the decoupling member 11'. Unlike the coupler of the second embodiment, however, the coupler sleeve 8' in that embodiment has been omitted. The coupler intermediate member 7' is directly in an engagement with the coupler output member 9 which transfers the rotational drive movement of the coupler input member 6' onto the coupler output member 9.

A dosage display 20" is coupled to the coupler input member 6' via a display coupling member 23 and, like the display coupling members 21 and 22 of the other embodiments above, is connected to the coupler input member 6', such that it is secured against rotating. The display coupling member 23 cannot be moved in and counter to the direction of the coupler movement X relative to the casing part 4. As in the first and second embodiments, the rotationally secured connection of the display coupling member 23 exists both in the decoupled and in the coupled state of the device.

For setting the dosage and during storage, to prevent the coupler input member 6' from the rotational drive movement and to hold the drive member 25 in its tensed state, a rotational block is formed between the coupler casing 6' and the casing part 4. In the holding position of the coupler members 6', 7' and 9 shown, the rotational block exists between a first blocking member 24 and a second blocking member 34. The blocking member 24 is connected to the coupler input member 6', such that it is secured against rotating. The blocking member 34 is connected to the casing part 4, such that it is secured against rotating but can be moved in and counter to the direction of the coupler movement X relative to the casing part 4 and the coupler input member 6'. The facing areas of the blocking members 24 and 34, which contact each other in the blocking engagement, form a ratchet which allows a rotational movement of the coupler input member 6' which tenses the drive member 25, and prevents a rotational movement in the opposite direction.

Figure 23:
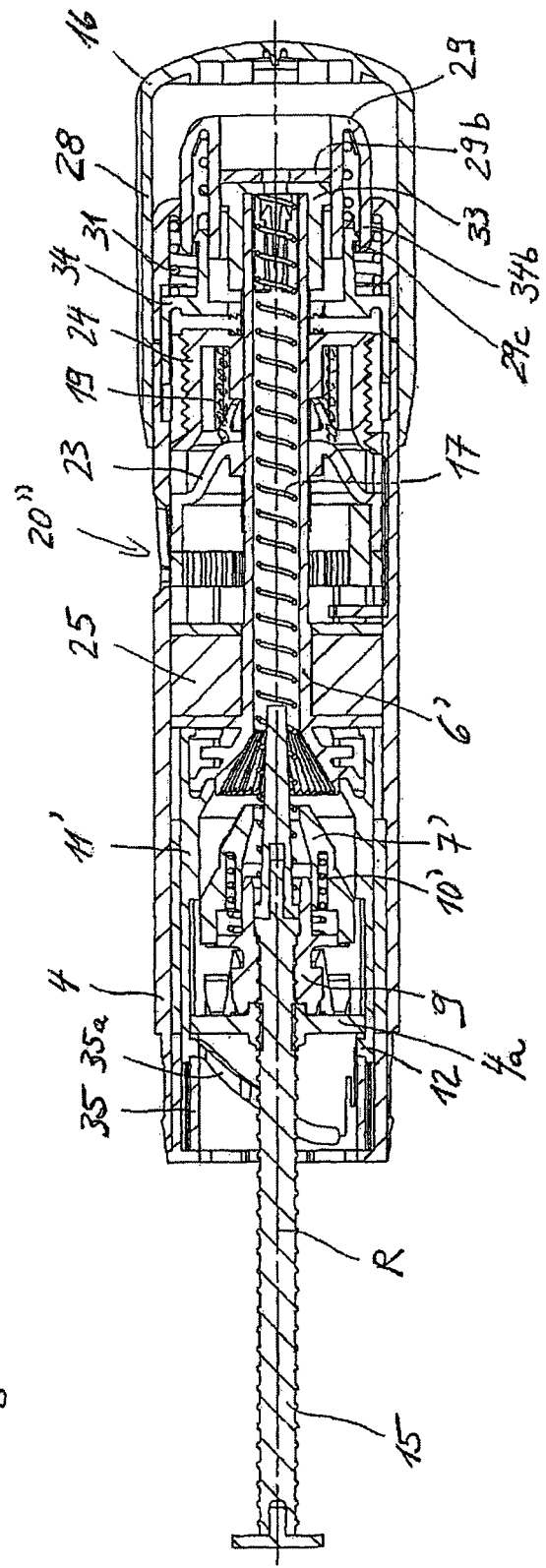
FIG. 23 shows the proximal part of the injection apparatus of FIG. 19, after the reservoir has been emptied.
Figure 24:
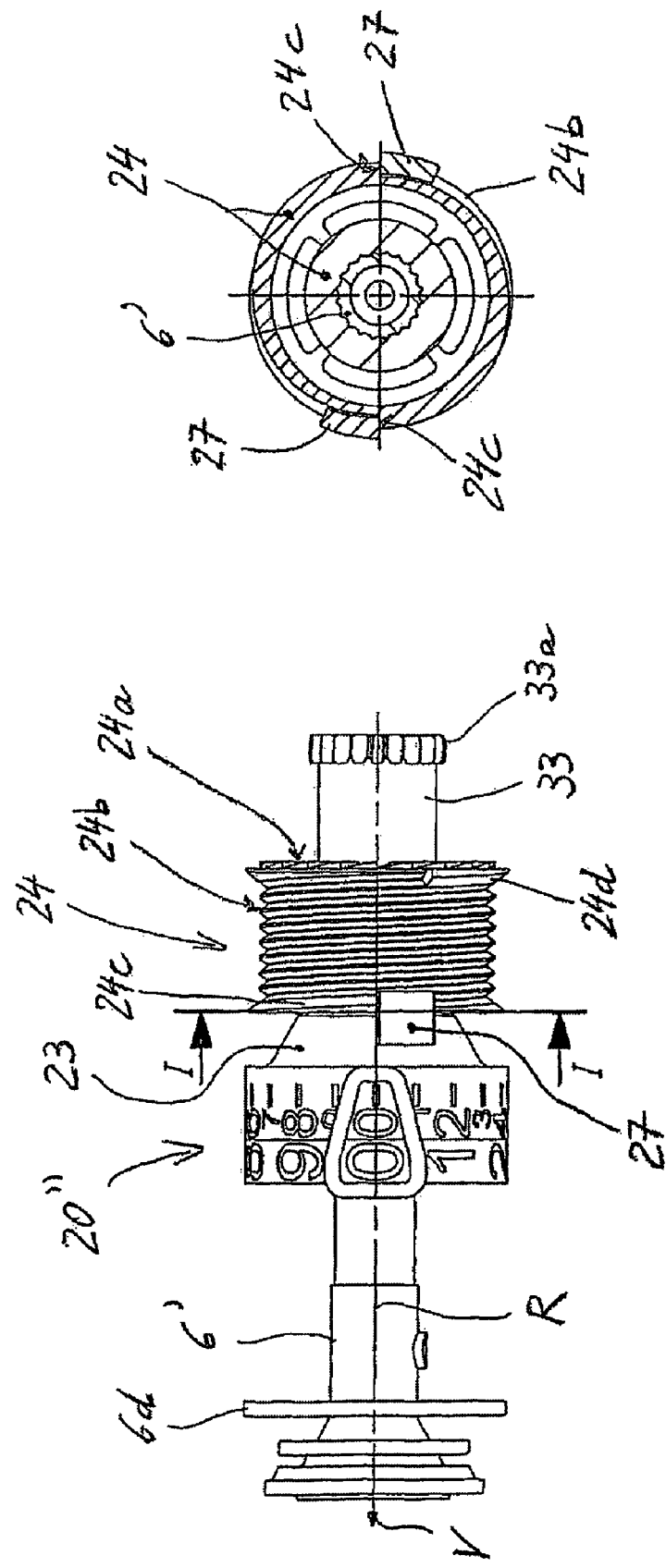
FIG. 24 shows a blocking member and a stopping member of FIG. 19.

FIG. 24 shows the coupler input member 6' together with the blocking member 24 mounted or carried on it, such that it is secured against rotating, the display coupling member 23 connected to the coupler input member 6', such that it is secured against rotating, and a connecting part 33 connected to the input member 6' such that it cannot be moved. The display coupling member 23 forms a units counting ring of the dosage display 20" and is suitably coupled to a tens counting ring to display the dosage set. On a proximal facing side facing the blocking member 34, the blocking member 24 is provided with blocking teeth 24a which are arranged evenly about the axis R and, in the blocking engagement, co-operate with counter teeth of the blocking member 34, to form the rotational block with respect to the drive movement. For a second function connected with dosing and delivery, a shell outer area of the blocking member 24 is provided with a thread 24b, the threaded axis of which coincides with the threaded axis R of the piston rod 15. A stopping member 27 engages with the thread 24b. The stopping member 27 is guided such that it can be linearly moved parallel to the threaded axis R; in the embodiment, in an axial groove on the inner shell area of the casing part 4. The blocking member 24 forms a rotational stopper 24c for the stopping member 27, which limits the drive movement of the coupler input member 6' which advances the piston rod 15. It forms another rotational stopper 24d for the stopping member 27, which determines the maximum dosage which can be delivered and set. Another stopping member 27 is arranged on the other side of the threaded axis R, opposite the stopping member 27 which can be seen in the view in FIG. 23, and co-operates in the same way with two other rotational stoppers 24c and 24d. The thread 24d is double-threaded. The stopping members 27 simultaneously abut against the respectively assigned rotational stoppers 24c and 24d, as can be seen in the cross-sectional representation in FIG. 23 for the rotational stoppers 24c. The rotational stoppers 24c determine a zero dosage position and the rotational stoppers 24d determine a maximum dosage position.

In the third embodiment, the holding means is formed in a third variant. It includes a restoring member 19, as well as the display coupling member 23 and the blocking member 24. The restoring member 19 is supported on the casing part 4 via the display coupling member 23 in the direction of the coupler movement X and on the blocking member 24 counter to the direction of the coupler movement X. The restoring member 19 presses the blocking member 24 until it abuts against the connecting part 33. Since the connecting part 33 is connected to the coupler input member 6' such that it cannot be moved in and counter to the direction of the coupler movement X, the restoring member 19 thus exerts an elastic restoring force, acting counter to the direction of the coupler movement X, on the coupler input member 6' via the blocking member 24 and the connecting part 33, said elastic restoring force holding the coupler input member 6' in the holding position retracted out of the coupler engagement. It again acts as a pressure spring. The blocking member 24 is a sleeve part comprising an outer shell forming the thread 24b, an inner shell serving to mount it on the coupler input member 6' such that it is secured against rotating, and a base which connects the two shells and on which the blocking teeth 24a are formed. The restoring member 19 protrudes into the blocking member 24 which is cup-shaped in this way, and is supported on the base of the blocking member 24.

The restoring member 19 presses the blocking member 24 not only until it abuts against the connecting part 33, but also until it abuts against the casing part 4. Abutting in this other way prevents the blocking member 24 from being able to move counter to the direction of the coupler movement X beyond the holding position assumed in FIG. 20. The blocking member 24 can thus be moved relative to the coupler input member 6', against the restoring elasticity force of the restoring member 19, in the direction of the coupler movement X. Conversely, the coupler input member 6' can be moved counter to the direction of the coupler movement X relative to the blocking member 24 abutting against the casing part 4.

The equalizing spring 17, tensed between the piston rod 15 and the connecting part 33, supports the restoring member 19 in its function of holding the coupler input member 6' in the holding position. The equalizing spring 17 could in principle replace the restoring member 19 for retracting the coupler members 6', 7' and 9. In some preferred embodiments, however, it is weak enough that, at least once it has been partially relaxed, it can no longer hold the coupler members 6'-9 in the holding position, and thus can no longer hold the coupler in the decoupled state.

A triggering element 28 is provided for triggering the drive member 25. The triggering element 28 can be moved translationally relative to the casing part 4 in the direction of the coupler movement X—in this embodiment, the advancing direction V and/or distal direction—and rotationally about the rotational axis R of the coupler input member 6', which coincides with the threaded axis R of the piston rod 15, and is guided in these two movements by the casing part 4. The translational movement in the distal direction establishes the coupler engagement between the coupler input member 6' and the coupler intermediate member 7' and releases the rotational block between the blocking members 24 and 34, which triggers the drive member 25, i.e. delivery. The translational movement in the advancing direction V is therefore also referred to in the following as the triggering movement.

In another function, the triggering element 28 forms the dosing member of the third embodiment. Via multiple intermediate members, the rotational movement of the triggering element 28 relative to the casing part 4 sets the product dosage which can be delivered by the next delivery process. This movement is also referred to in the following as the dosing movement. From the zero dosage position, which is shown in FIG. 20 and determined by the stopping members 27 abutting the rotational stoppers 29c of the blocking member 24 which limit the drive movement of the coupler input member 6', the dosage can be set by rotating the triggering element 28 in the direction of the rotational direction arrow indicated, the dosing direction. The rotational dosing movement of the triggering element 28 is transferred onto the coupler input member 6' via an inner part 29—which is connected to the triggering element 28 such that it is secured against rotating and shifting or is formed integrally with it—and the connecting part 33. For transferring, the inner part 29 and the connecting part 33 are in an engagement with each other, such that they are secured against rotating, and the connecting part 33 is connected to the coupler input member 6', such that it is secured against rotating. For securing against rotating, the inner part 29 and the connecting part 33 are provided with an inner toothing 29a and an outer toothing 33a which interlock with each other in the resting state of the apparatus and can be axially shifted with respect to each other.

The triggering element 28 is arranged in the proximal end region of the casing part 4 so as to be user-friendly. Its outer sleeve part surrounds the casing part 4. A base of the triggering element 28 forms a proximal end of the injection apparatus. For setting the dosage, the triggering element 28 can be operated as a turning button and is ribbed on its outer shell area for this purpose. For triggering, it can be operated as a push button. During the dosing movement, the triggering element 28 locks with the casing part 4 in discrete rotational angular positions corresponding to the dosage units.

A stopper element 29b facing a proximal facing area of the connecting part 33 projects radially inwards from the inner part 29. In the resting state of the apparatus, a clear distance remains between the connecting part 33 and the stopper element 29b, said clear distance being just large enough that the rotational block between the inner part 29 and the connecting part 33 is released during the triggering movement of the triggering element 28, before the stopper element 29b terminates the relative movement of the triggering element 28 relative to the connecting part 33 by an abutting contact.

The second blocking member 34 is tensed in the blocking engagement with the blocking member 24 by a blocking spring 31. For this purpose, the blocking spring 31 is supported in the direction of the coupler movement X on the blocking member 34 and counter to the coupler movement X on a casing part 30 which is fixedly connected to the casing part 4. Another spring 32, arranged between the inner part 29 and the blocking member 34, tenses the triggering element 28 relative to the blocking member 34 into a proximal end position. The blocking member 34 is axially guided, such that it is secured against rotating, by the casing part 4. The casing part 4 forms a distal and a proximal stopper for the mobility of the blocking member 34.

In the resting state shown in FIG. 20, the user sets the dosage by rotating the triggering element 28 in the dosing direction. During this rotational dosing movement, the triggering element 28 slaves the connecting part 33 via the rotational block 29a, 33a, and the connecting part 33 for its part slaves the coupler input member 6' which thus completes the same rotational dosing movement as the triggering element 28. Rotating the coupler input member 6' tenses the drive member 25. In engagement with the thread 24b of the blocking member 24, the stopping member 27 migrates from the stopper 24c of the thread 24b which determines the zero dosage, in the direction of the stopper 24d which determines the maximum dosage (FIG. 24).

Figure 22:
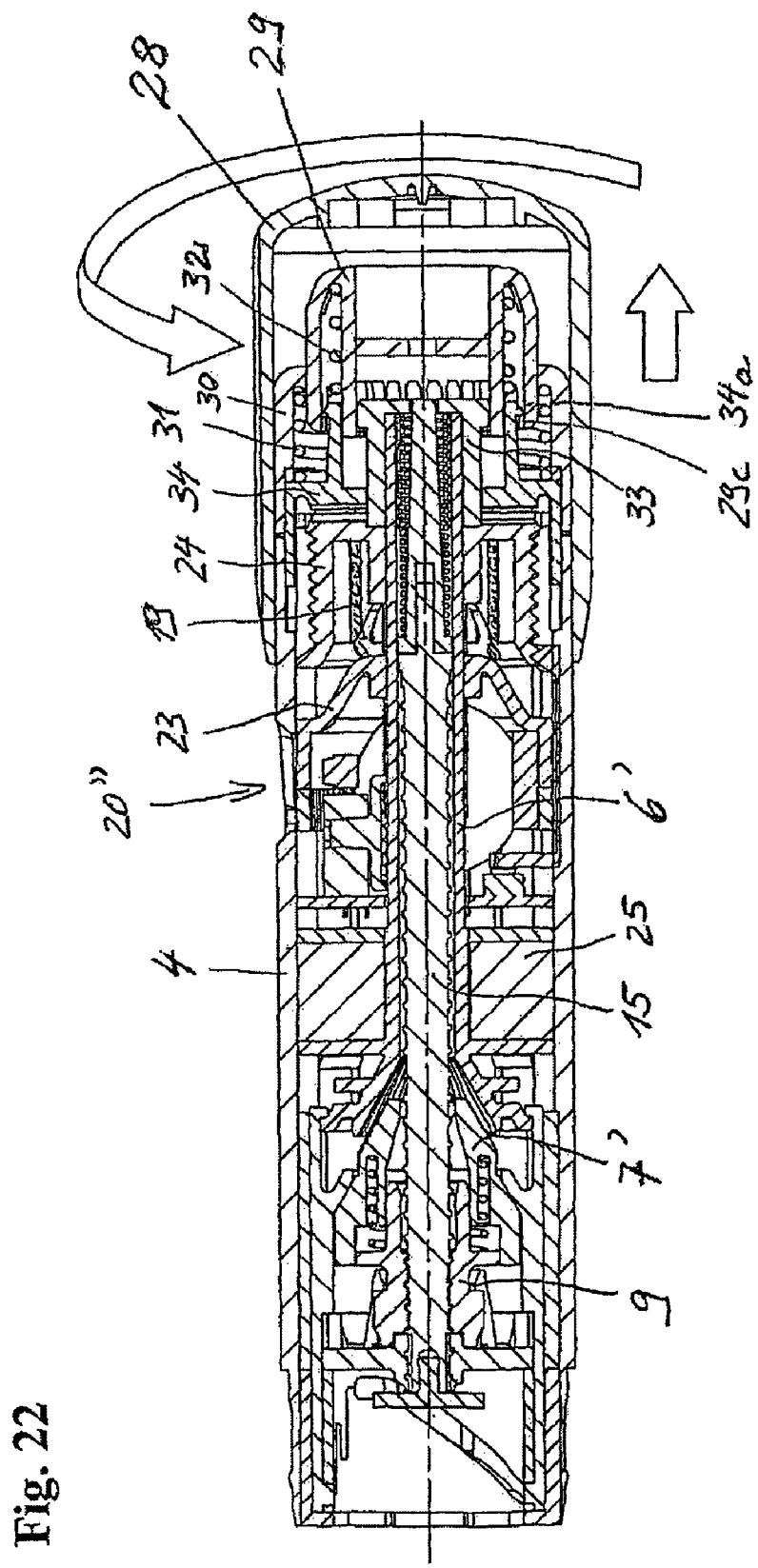
FIG. 22 shows the proximal part of the injection apparatus of FIG. 19, when correcting the dosage.

The injection apparatus also offers a convenient way of correcting the dosage, as is clear from a comparison of FIGS. 20 and 22. If the user has inadvertently set too high a dosage, he/she can correct the dosage by rotating the coupler input member 6' back. For correcting the dosage, the user pulls the triggering element 28 in the proximal direction. This retracting movement of the triggering element 28 is indicated in FIG. 22 by an arrow, as is the rotational direction for correcting. In the resting state of the apparatus, the inner part 29 and the blocking member 34 are in a slaving engagement with respect to a movement in the proximal direction. The corresponding slaving means are indicated as 29c and 34a. The slaving means 29c formed by the inner part 29 and the slaving means 34a formed by the blocking member 34 grip behind each other and form a latch for the retracting movement of the triggering element 28. Pulling on the triggering element 28 thus also moves the blocking member 34 in the proximal direction, against the force of the blocking spring 31, thus releasing it from the blocking engagement with the blocking member 24 which abuts against the casing part 4. As soon as the rotational block is released, the user can correct the dosage by means of a reverse rotational movement of the triggering element 28 and the still extant rotationally secured engagement between the inner part 29 and the connecting part 33. As soon as the user releases the triggering element 28, it snaps back in the distal direction together with the blocking member 34 due to the effect of the blocking spring 31, and the blocking member 34 thus snaps back into the blocking engagement with the blocking member 24. During the reverse rotational movement, the user expediently continues to hold the triggering element 28 fast, which is facilitated by the rotational angular locking positions of the triggering element 28. In principle, however, the user can also let it snap back and re-dose, as applicable.

Once the desired dosage has been set, the apparatus is placed onto the skin at the desired administering location, and the injection needle is injected. For injecting the needle, the triggering element 28 takes on another function, for which purpose it is coupled to the needle protection 39 (FIG. 19).

In a first phase of injecting, the user presses the injection apparatus against the skin, such that the needle protection 39 is moved in the distal direction relative to the casing part 38. However, this first part of the movement of the needle protection 39 does not yet expose the injection needle; rather, its tip remains short of the needle protection 39. In this first phase of the injecting process, the needle protection 39 abuts against a resisting element, such that it cannot be moved further in the distal direction relative to the casing part 38. While continuing to exert pressure on the injection apparatus in the direction of the skin, the user presses the triggering element 28 in the proximal direction. In the course of this first phase of its triggering movement, the triggering element 28 releases an abutting contact between the needle protection 39 and the resisting element, such that the injection apparatus, and together with it the injection needle, are moved relative to the needle protection 39 in the direction of the skin, and the injection needle injects. With respect to the function of the triggering element 28 for injecting the needle, reference may be made to a patent application "Attachment Module for an Injection Device Comprising an Engagement Control for a Needle Covering Element" owned by the owner of the present application.

As soon as the injection needle has been subcutaneously placed, the drive member 25 can be released and the product delivered by pressing further onto the triggering element 28. In the second phase of the triggering movement of the triggering element 28, which follows the injection phase, the triggering element 28 and therefore the inner part 29 is pressed further in the distal direction relative to the connecting part 33, against the pressure of the spring 32, such that the rotational block 29a, 33a is released. The triggering element 28 can rotate idly. As soon as the rotational block 29a, 33a has been released, the stopper element 29b passes into abutting contact with the connecting part 33. In the third phase of the triggering movement which then follows, the triggering element 28 presses the connecting part 33 and therefore the coupler input member 6' via the stopper element 29b, in the direction of the coupler movement X; in the embodiment, in the advancing direction V. Due to the effect of the spring force of the blocking spring 31, the blocking member 34 follows this movement until it abuts against the casing part 4. Before the blocking member 34 reaches the abutting position, the coupler input member 6' passes into the coupler engagement with the coupler intermediate member 7'. The coupler input member 6' presses the coupler intermediate member 7' out of the frictional-lock blocking engagement with the decoupling member 11', against the force of the restoring member 10'. Once the blocking engagement between the conical areas of the two members 7' and 11' has been released and the coupler engagement therefore completely established, the blocking member 34 abuts the casing part 4. In the final phase of the triggering movement which then follows, the triggering element 28 presses the blocking member 24 out of the blocking engagement with the blocking member 34 via the connecting part 33.

As soon as the rotational block formed by the blocking members 24 and 34 is released, the rotational drive movement of the coupler input member 6' is initiated due to the drive force of the drive member 25 and is transferred onto the coupler output member 9 via the coupler engagement. Because it is guided,—such that it is secured against rotating—in the linear guide 4a, the piston rod 15 is moved—in the threaded engagement with the coupler output member 9—in the advancing direction V, and product is delivered. This delivery movement is terminated by the stopping member 27 abutting the stopper 24c of the blocking member 24 which determines the zero dosage.

FIG. 21 shows the injection apparatus when a zero dosage or a small priming dosage is set, in the coupled state after the rotational block 24, 34 has been released, i.e. after the triggering element 28 has completely performed the triggering movement. If, advantageously, pressure is continuously exerted on the triggering element 28, the triggering sequence described above progresses automatically, from injecting to completely delivering the dosage set.

FIG. 23 shows the injection apparatus after the container 2 has been emptied. The casing part 1 has already been removed from the casing part 4. The piston rod 15 assumes its most distal position. The decoupling member 11' blocks the coupler input member 6' in the position retracted from the coupler intermediate member 7'. The functionality of the decoupling member 11' corresponds to that in the other embodiments. Unlike the two first embodiments, however, the casing part 1 and the decoupling member 11' are not directly in a guiding engagement with each other, but rather via an adaptor structure 36. The adaptor structure 36 is a sleeve in the casing part 4 which is fixed in and counter to the direction of the coupler movement X in the connecting portion, but can be rotated about the central longitudinal axis R of the casing part 4. The adaptor structure 35 forms a guiding curve 36a either as a cavity on or a breach in its shell area facing the decoupling member 11'. The guiding curve 35a exhibits the course of a threaded portion. The length measured over the circumference and the pitch of the guiding curve 35a measured with respect to the central longitudinal axis of the casing part 4 are dimensioned such that the decoupling member 11' is moved into the decoupling position shown in FIG. 21 by a quarter to a half revolution of the adaptor structure 35 relative to the decoupling member 11'. For generating the axial movement, the decoupling member 11' engages via its engaging element 12 with the guiding curve 35a. In this respect, reference is made to the statements regarding the first embodiment.

When connecting the casing parts 1 and 4, the adaptor structure 35 forms a linear guide for the casing part 1. The casing part 1 is inserted into the adaptor structure 35, wherein a slight frictional lock and correspondingly a sliding guide for the casing part 1 exists. The casing part 1 cannot be rotated about the central longitudinal axis of the casing part 4 relative to the adaptor structure 35. The engagement, which is rotationally secured accordingly, is established right at the beginning of inserting the casing part 1 into the adaptor structure 35. Once the casing part 1 has been inserted until it abuts against the casing part 4, i.e. once the coupler is accommodated at 4a, the casing part 1 is rotated relative to the casing part 4 and slaves the adaptor structure 36 during this rotational movement, until the engaging element 12 of the decoupling member 11' abuts the end of the guiding curve 36a. The rotational movement of the casing part 1 is not possible until its axial abutting position, for which purpose a rotational block acting up until the abutting position can also be formed between the casing parts 1 and 4.

The movement of the decoupling member 11' caused in the guiding engagement exhibits an axial length which is greater than the length X of the complete coupler movement. In its decoupling movement, the decoupling member 11' presses the coupler input member 6' beyond its holding position as assumed in the resting state, and blocks it in said decoupling position. In this forced decoupling movement, the coupler input member 6' slaves the triggering element 28 via the stopper element 29b. Via the latch between the slaving means 29c and 34a, the blocking member 34 is also slaved, against the force of the blocking spring 31, and moved out of the blocking engagement. The blocking member 24 cannot follow the blocking member 34, since it is abutting against the casing part 4. Detaching the casing parts 1 and 4 thus releases the rotational block by means of the decoupling mechanism which the casing parts 1 and 4 form with the decoupling member 11' via the adaptor structure 35. If the coupler input member 6' has not yet assumed the zero dosage position, it is rotated now at the latest into the zero dosage position by the drive member 25, and the dosage display 20" is zeroed. In this respect, reference may again be made to the particular advantage of the coupling between the dosage display 20" and the coupler input member 6', namely that for each delivery, the dosage display 20" is reset in accordance with the delivered dosage. If, one time, the dosage set was not delivered, for because the injection process was aborted or the container 2 no longer contained the complete dosage set, the user can read this from the dosage display 20" which is then only partially reset.

Embodiments of the present invention, including preferred embodiments, have been presented for the purpose of illustration and description. They are not intended to be exhaustive or to limit the invention to the precise forms and steps disclosed. The embodiments were chosen and described to provide the best illustration of the principles of the invention and the practical application thereof, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A device for administering a fluid product comprising a housing, a conveying device for the product, a coupling element provided for the drive of the conveying device and which can be rotated about a rotational axis, a first blocking member connected in a rotationally secure manner to the coupling element, a second blocking member detachably engageable with the first blocking member thereby preventing a rotational movement thereof in the drive direction and enabling said rotational movement to take place in the counter dosing direction, a torsion spring connected to the coupling element such that it is stressed by the rotational movement when the blocking members are engaged in a blocked position and drives the coupling element in a rotary manner after the blocking position is released, and a release element coupled to at least one of the blocking members such that a release movement of the release element translationally along the rotational axis displaces at least one of the blocking members from the blocked position, the release element also forming a dose setting element used to set a product dose amount to be delivered.

2. A device for administering a fluid product, said device including:
   a) a casing comprising a reservoir for the product;
   b) a conveying means for the product;
   c) a coupler member rotationally moveable about a rotational axis for driving the conveying means;
   d) a first blocking member connected to the coupler member so that the first blocking member is slaved in rotation by the coupler member;
   e) a second blocking member which, in a releasable blocking engagement with the first blocking member, prevents a rotational movement of the first blocking member in a drive direction and allows the rotational movement of the first blocking member in an opposite dosing direction;
   f) a torsion spring which is connected to the coupler member such that it is tensed by the rotational movement when the blocking members are in blocking engagement, and rotationally drives the coupler member after the blocking engagement is released; and
   g) a triggering element coupled to at least one of the blocking members such that a triggering movement of the triggering element moves said at least one of the blocking members out of the releasable blocking engagement;
   h) wherein the triggering element also comprises a dosing member for setting a product dosage to be delivered.

3. The device according to claim 2, wherein the coupler member drives the conveying means as the coupler member moves by a coupler movement in a direction parallel to the rotational axis into a coupler engagement with the conveying means, wherein the blocking engagement is released by the coupler movement.

4. The device according to claim 3, wherein the coupler movement is a translational movement along the rotational axis.

5. The device according to claim 4, wherein the coupler member slaves one of the blocking members during the coupler movement, which releases the blocking engagement.

6. The device according to claim 2, wherein the triggering element is coupled to the coupler member such that the triggering movement of the triggering element causes a coupler movement of the coupler member in a direction parallel to the rotational axis into a coupler engagement in which a drive force of the torsion spring is transferred to the conveying means via the coupler member.

7. The device according to claim 6, wherein the triggering element slaves the coupler member during the triggering movement.

8. The device according to claim 2, wherein the coupler member is rotationally coupled to the conveying means in a first phase of the triggering movement, and in a second phase of the triggering movement, the blocking engagement of the blocking members is released, while the coupling between the coupler member and the conveying means is extant.

9. The device according to claim 6, wherein the second blocking member can be moved in the direction of the coupler movement.

10. The device according to claim 2, further comprising a blocking spring that urges one of the blocking members into the blocking engagement.

11. The device according to claim 2, further comprising a blocking spring acting on the second blocking member in the direction of the coupler movement.

12. The device according to claim 2, wherein the coupler member performs a dosing rotational movement in the dosing direction when the product dosage is being set.

13. The device according to claim 12, wherein the triggering element performs a rotational dosing movement when the product dosage is being set, and is coupled to the coupler member such that rotational dosing movement of the triggering element causes the dosing rotational movement of the coupler member.

14. The device according to claim 13, wherein the triggering element is connected to the coupler member and slaves the coupler member in rotation when setting the product dosage.

15. The device according to claim 13, wherein the coupling between the triggering element and the coupler member for setting the product dosage is releasable.

16. The device according to claim 12, further comprising a dosage display coupled to the coupler member such that the dosing rotational movement causes an increase in a dosage value displayed.

17. The device according to claim 12, further comprising a dosage display coupled to the coupler member such that a movement of the coupler member in the drive direction causes a reduction in a dosage value displayed.

18. The device according to claim 2, wherein the torsion spring is a spiral spring wound around the rotational axis, comprising an inner spring winding and at least one outer spring winding which surrounds the inner spring winding over at least a part of its circumference.

19. The device according to claim 18, wherein one end of the torsion spring is connected, secure against rotating, to the coupler member.

20. The device according to claim 18, wherein the coupler member mounts the torsion spring and the torsion spring is slaved in a coupler movement of the coupler member in a direction along the rotational axis.

21. The device according to claim 20, wherein the torsion spring does not exert a force on the coupler member in the direction of the coupler movement, or exerts a force acting counter to the coupler movement.

22. The device according to claim 3, further comprising a holding means which holds the coupler member in a holding position, decoupled from the conveying means prior to establishing the coupler engagement.

23. The device according to claim 22, wherein the holding means comprises a restoring member and the restoring member charges the coupler member with an elastic restoring force acting counter to the coupler movement.

24. The device according to claim 23, wherein the restoring member is supported counter to the coupler movement on the first blocking member.

25. The device according to claim 2, wherein for correcting a dosage, the triggering element performs a retracting movement in a direction opposite a triggering movement direction which releases the blocking engagement of the blocking members.

26. The device according to claim 25, wherein the triggering element is coupled to the second blocking member such that the retracting movement causes a movement of the second blocking member out of the blocking engagement.

27. The device according to claim 2, wherein the coupler member can be moved relative to the first blocking member counter to the direction of the coupler movement, a restoring member charges the first blocking member with an elastic restoring force acting counter to the coupler movement, and wherein the casing or a structure connected to the casing forms a stopper, which acts counter to the elastic restoring force, for the first blocking member.

28. The device according to claim 2, wherein the casing includes a first casing part comprising the reservoir, and a second casing part which carries the coupler member and the blocking members, and wherein the casing parts are detachable from each other and the device comprises a decoupling mechanism which, while acting on at least one of the blocking members, automatically releases the blocking engagement when the casing parts are detached.

29. The device according to claim 28, wherein the decoupling mechanism moves the coupler member counter to the direction of the coupler movement, and the coupler member is coupled to the second blocking member during said movement of the coupler member, such that the second blocking member is moved counter to the direction of the coupler movement, out of the blocking engagement.

30. The device according to claim 2, wherein the first blocking member forms a first rotational stopper which limits the rotational movement of the coupler member in the drive direction.

31. The device according to claim 2, wherein the first blocking member forms a second rotational stopper which limits the rotational movement of the coupler member in the dosing direction.

32. The device according to claim 30, wherein the first blocking member is provided with a thread and the device includes a stopping member which in the course of the rotational movement abuts against the rotational stopper and so limits the rotational movement.

33. The device according to claims 31, wherein the first blocking member is provided with a thread and the device includes a stopping member which in the course of the rotational movement abuts against the rotational stopper and so limits the rotational movement.

34. The device according to claim 2, wherein the first blocking member and the coupler member can be moved relative to each other along the rotational axis, and a restoring member charges the first blocking member with an elastic restoring force in the direction of the second blocking member.

35. The device according to claim 34, wherein the first blocking member is a sleeve body comprising a base, and the restoring member is supported on the base and protrudes into the sleeve body.

36. The device according to claim 3, wherein the first blocking member can be moved counter to the direction of the coupler movement until it abuts against at least one of the coupler member and the casing.

* * * * *